US007026943B2

(12) United States Patent
Knowles et al.

(10) Patent No.: US 7,026,943 B2
(45) Date of Patent: Apr. 11, 2006

(54) ACOUSTIC WAVE ICE AND WATER DETECTOR

(75) Inventors: Terence J. Knowles, Barrington, IL (US); Chris Kalmus, LaGrange, IL (US)

(73) Assignee: TexZec, Inc., Round Rock, TX (US)

( * ) Notice: Subject to any disclaimer, the term of this patent is extended or adjusted under 35 U.S.C. 154(b) by 0 days.

(21) Appl. No.: 10/611,457

(22) Filed: Jul. 1, 2003

(65) Prior Publication Data

US 2005/0016278 A1   Jan. 27, 2005

(51) Int. Cl.
*G08B 19/02*   (2006.01)
(52) U.S. Cl. .................. 340/582; 340/580; 340/693.6; 73/573; 73/579; 73/589; 73/645; 73/650; 73/659; 367/137; 367/162
(58) Field of Classification Search ............... 340/580, 340/582; 73/572, 579, 589, 599, 650, 658, 73/659, 170.26; 367/162, 137
See application file for complete search history.

(56) References Cited

U.S. PATENT DOCUMENTS

| | | | |
|---|---|---|---|
| 3,540,265 A * | 11/1970 | Lynnworth | ................... 73/627 |
| 4,461,178 A | 7/1984 | Chamuel | |
| 4,604,612 A | 8/1986 | Watkins et al. | |
| 4,645,870 A | 2/1987 | Adler | |
| 4,700,176 A | 10/1987 | Adler | |
| 4,893,496 A * | 1/1990 | Bau et al. | .................... 73/32 A |
| 5,051,645 A * | 9/1991 | Brace et al. | ............ 310/313 D |
| 5,095,754 A * | 3/1992 | Hsu et al. | ..................... 73/602 |
| 5,149,986 A | 9/1992 | Jalbert | |
| 5,159,838 A * | 11/1992 | Lynnworth | ................... 73/644 |
| 5,177,327 A | 1/1993 | Knowles | |
| 5,451,723 A | 9/1995 | Huang et al. | |

(Continued)

OTHER PUBLICATIONS

"Trapped Torsional Modes In Solid Cylinders", W. Johnson, B.A. Auid, and E. Segal, J. Acoust. Soc. Am. 100 (1), Jul. 1996.

*Primary Examiner*—Benjamin C. Lee
(74) *Attorney, Agent, or Firm*—McAndrews, Held & Malloy, Ltd.

(57) ABSTRACT

An acoustic wave sensor utilizes one or more acoustic waves trapped in an acoustic wave cavity to detect the presence of one or more substances on a surface of the acoustic wave cavity. To detect the presence of ice, a trapped torsional acoustic wave is used. To detect water, an acoustic wave with flexural or compressional components is used. The sensor includes a number of transducers adjacent the acoustic wave cavity where a controller drives different sets of the transducers to generate different acoustic waves.

82 Claims, 10 Drawing Sheets

U.S. PATENT DOCUMENTS

| | | | |
|---|---|---|---|
| 5,456,114 A * | 10/1995 | Liu et al. ................. 73/597 |
| 5,573,077 A | 11/1996 | Knowles |
| 5,629,485 A | 5/1997 | Rose et al. |
| 5,673,041 A | 9/1997 | Chatigny et al. |
| 5,813,280 A | 9/1998 | Johnson et al. |
| 5,856,820 A | 1/1999 | Weigers et al. |
| 5,922,958 A * | 7/1999 | Schugt ................. 73/596 |
| 5,986,224 A | 11/1999 | Kent |
| 6,078,315 A | 6/2000 | Huang |
| 6,085,576 A | 7/2000 | Sunshine et al. |
| 6,087,599 A | 7/2000 | Knowles |
| 6,091,406 A | 7/2000 | Kambara et al. |
| 6,286,370 B1 * | 9/2001 | Sinha ................. 73/579 |
| 6,369,806 B1 | 4/2002 | Endo et al. |
| 6,378,377 B1 | 4/2002 | Matuseski et al. |
| 6,473,075 B1 | 10/2002 | Gomes et al. |

* cited by examiner

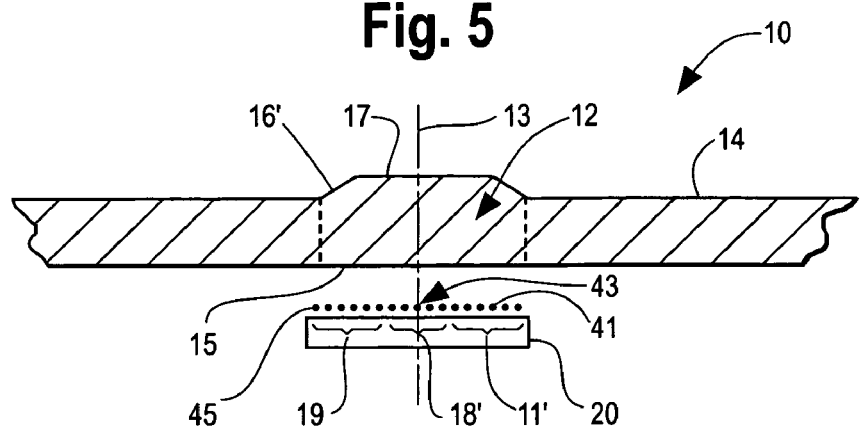
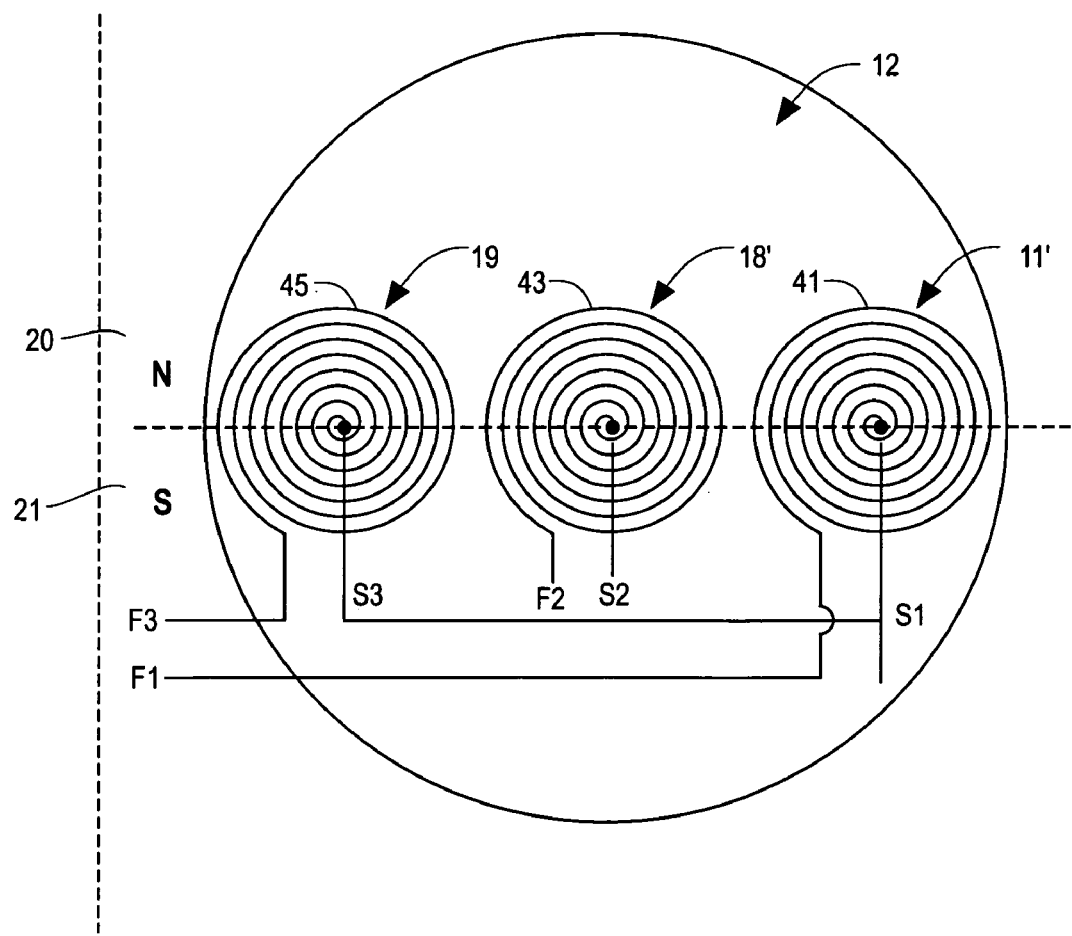

Fig. 9
Fig. 10A
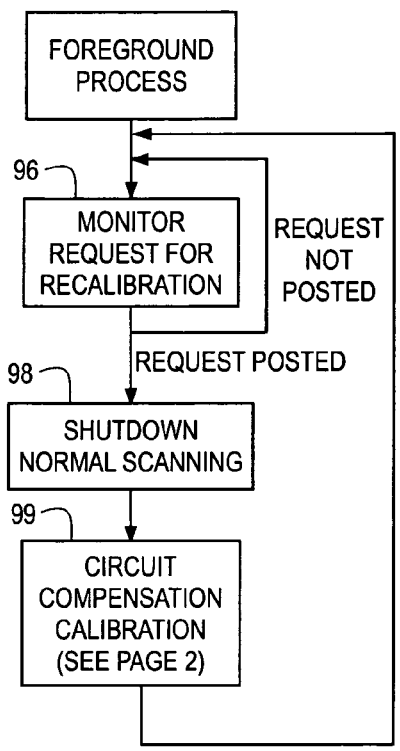
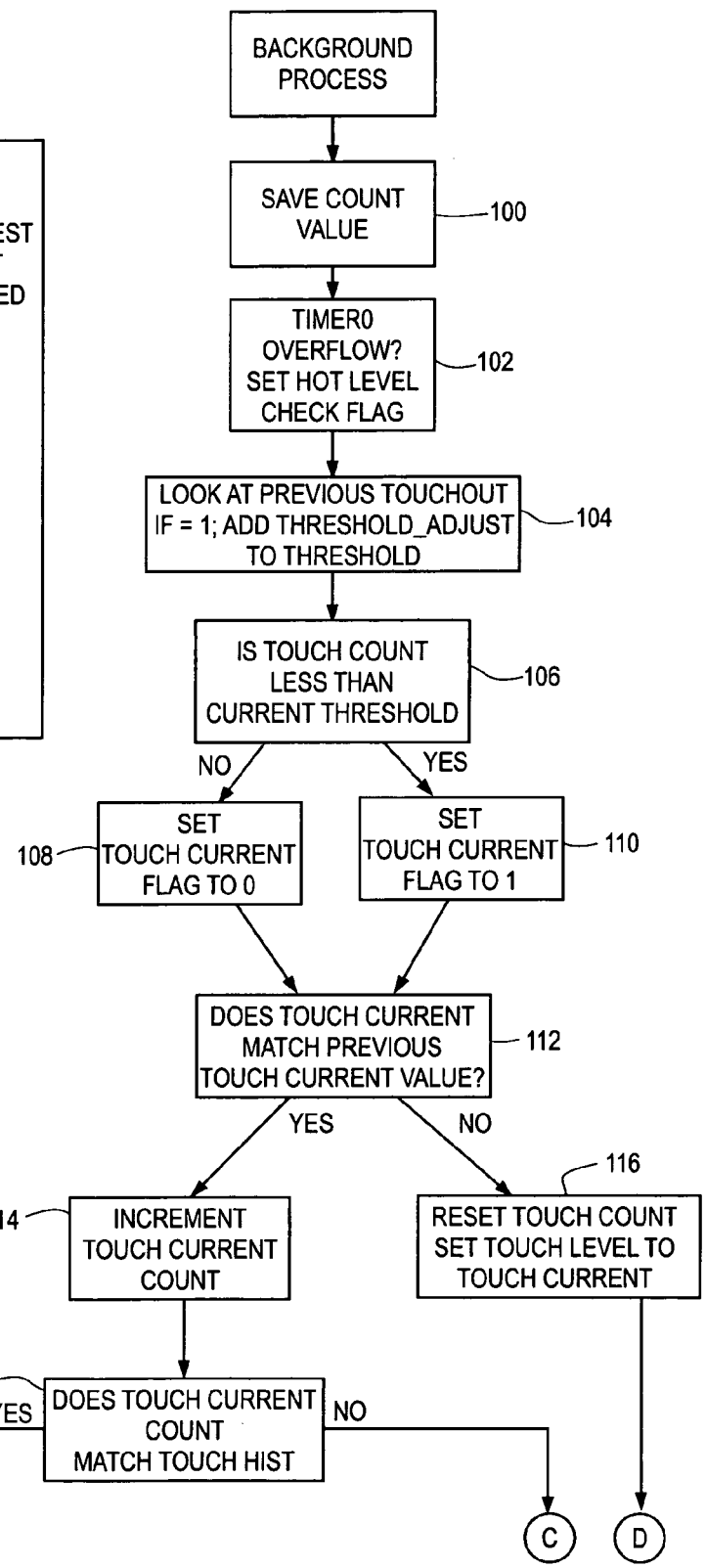

ACOUSTIC WAVE ICE AND WATER DETECTOR

CROSS-REFERENCE TO RELATED APPLICATIONS

This application is related to U.S. patent application entitled "Torsional Acoustic Wave Sensor," Ser. No. 10/611,583, filed concurrently herewith and U.S. patent application entitled "Acoustic Wave Touch Detection Circuit and Method," Ser. No. 10/454,003, filed Jun. 4, 2003.

STATEMENT REGARDING FEDERALLY SPONSORED RESEARCH OR DEVELOPMENT

N/A

FIELD OF INVENTION

The present invention relates to an acoustic wave sensor utilizing one or more acoustic waves trapped in an acoustic wave cavity for detecting the presence of one substance or more than one substance on the surface of the cavity. In one embodiment, the acoustic wave sensor forms an ice detector and in another embodiment, the sensor forms and ice and water detector although the acoustic wave sensor of the present invention can be used to sense the presence of other substances as well.

BACKGROUND OF THE INVENTION

Ice detectors are known that utilize acoustic waves propagating over a distance through a structure, such as the outer material of an airplane wing, wherein the acoustic waves propagate between a transmitter transducer and a receiver transducer. Propagating waves are used in these systems to detect the presence of ice along the length of the airplane wing structure through which the waves propagate as opposed to detecting ice at a localized spot. One such ice detector as shown in U.S. Patent, Chamuel U.S. Pat. No. 4,461,178 uses propagating flexural waves that are sensitive to water and ice. Another such sensor is shown in U.S. Patent, Watkins et al. U.S. Pat. No. 4,604,612 which uses propagating shear waves that are sensitive to ice but that are insensitive to water. U.S. Patent, Rose et al. U.S. Pat. No. 5,629,485 uses propagating guided waves and extracts various features from a frequency signature of the waves for classifying contaminants such as ice, water, glycol, oils and fuel. U.S. Patent, Matuseski U.S. Pat. No. 6,378,377 uses a propagating Lamb wave which is sensitive to ice and water. In one embodiment, instead of a separate receiver the system of this patent uses a reflecting strip positioned at a distance from a transceiver transducer where the reflecting strip reflects the Lamb waves back to the transducer for analysis. Because these systems use acoustic wave energy that propagates over a substantial length of an airplane wing, the analysis of the signal, representing the acoustic wave energy picked up by the receiver transducer, to determine the presence of ice or other contaminants is extremely complex. As a result, these systems are very expensive. When a maintenance check is performed, access to the interior of the airplane wing is required to access the ice detection system. This can be extremely difficult.

It is noted that although it was believed that an acoustic wave sensor utilizing a shear wave trapped in an acoustic wave cavity, such as described in U.S. patent application Ser. No. 09/998,355 filed Nov. 20, 2001, was insensitive to water like a shear wave propagating in a plate, it has been found that sensors utilizing a trapped shear wave are sensitive to water at a level that is a multiple of $\frac{1}{2}\lambda$, where $\lambda$ is the wavelength of the acoustic wave. It is believed that this sensitivity to water is due to flexural modes, that is a mode with a vertical displacement component, generated in the acoustic wave cavity with the trapped shear wave. More specifically, because the shear wave is trapped, particles are moving faster in the interior of the acoustic wave cavity than at the edge of the cavity. This results in a "bulge" of particles that creates a vertical component in the trapped acoustic wave in addition to the transverse shear component. It is this vertical component that causes flexural motion and makes the acoustic wave switch sensitive to water. As a result of this sensitivity, when the shear acoustic wave switch is used in the presence of water, the level of which varies, such as when the switch is used outdoors in rain, the water can cause the switch to have a response that flickers. Although this flicker problem can be overcome by software processing as disclosed in the co-pending patent application entitled "Acoustic Wave Touch Detection Circuit and Method," Ser. No. 10/454,003, filed Jun. 4, 2003, it is desirable to have an acoustic wave sensor and in particular an ice detector that is insensitive to water at any level so as to be able to detect the presence of ice alone.

It is noted that, besides the trapping of shear waves in a plate, it has been known that torsional waves could be trapped in a solid cylinder as described in the article "Trapped Torsional Modes In Solid Cylinders" by Ward Johnson, B. A. Auld and E. Segal, J. Acoust. Soc. Am. 100 (1), Jul. 1996. One application of a torsional mode trapped in a cylinder is an acoustic resonator for measuring force as shown in U.S. Pat. No. 5,813,280 to Johnson et al. However, the cylindrical body, in which the torsional wave is trapped, greatly limits the application and use of trapped torsional modes.

BRIEF SUMMARY OF THE INVENTION

In accordance with the present invention, the disadvantages of prior acoustic wave sensors, and in particular ice detectors, have been overcome. In accordance with the present invention, an acoustic wave sensor and method utilize one or more acoustic waves trapped in an acoustic wave cavity to detect the presence of one or more substances on a surface of the acoustic wave cavity. The senor of the present invention is simple to manufacture and inexpensive. Malfunctioning of the sensor can be detected from the sensor itself without a manual inspection of the sensor. Moreover, in accordance with one embodiment of the present invention, access to the sensor can be had from an external side of the member on which the sensor is mounted, for example an airplane wing.

In accordance with one embodiment of the present invention, an ice detector includes an acoustic wave cavity formed in a substrate and defined by an area of increased mass. At least one transducer is positioned adjacent the acoustic wave cavity so that when driven, the transducer generates in the acoustic wave cavity a trapped acoustic wave that is sensitive to ice and insensitive to water. The transducer also provides a signal representing the trapped acoustic wave in the acoustic wave cavity. A simple and inexpensive circuit is responsive to the transducer signal to detect the presence of ice. In one embodiment of the present invention, the transducer is positioned with respect to the acoustic wave cavity to generate a torsional acoustic wave that is trapped in the cavity.

In accordance with another embodiment of the present invention, the presence of different substances on an acoustic wave sensor is determined by: generating, in a first mode of operation, a first acoustic wave substantially trapped in an acoustic wave cavity formed in the sensor where the first acoustic wave is sensitive to a first substance on a surface of the acoustic wave cavity; generating, in a second mode of operation, a second acoustic wave different from the first acoustic wave, substantially trapped in the acoustic wave cavity formed in the sensor wherein the second acoustic wave is sensitive to a second substance on the surface of the acoustic wave cavity; and analyzing the response of the first and second acoustic waves to determine the presence of the first and/or second substances in the acoustic wave cavity.

In one embodiment of the present invention, the steps of generating the first and second acoustic waves in the acoustic wave cavity includes driving a first set of transducers positioned with respect to the acoustic wave cavity to generate the first acoustic wave and driving a second set of transducers positioned with respect to the acoustic wave cavity to generate the second acoustic wave.

In accordance with still another embodiment of the present invention, a method of detecting water and ice includes positioning a number of transducers with respect to an acoustic wave cavity; driving a first set of transducers to generate an acoustic wave trapped in the acoustic wave cavity wherein the acoustic wave trapped in the cavity is sensitive to ice and insensitive to water; providing a signal representing the acoustic wave generated by the first set of transducer; driving a second set of transducers to generate an acoustic wave trapped in the acoustic wave cavity wherein the acoustic wave trapped in the cavity is sensitive to water; providing a signal representing the acoustic wave generated by the second set of transducer; and analyzing the signals representing the acoustic waves generated by the first and second sets of transducers to detect the presence of ice/or water.

In accordance with a further embodiment of the present invention, an acoustic wave sensor includes an acoustic wave cavity formed in a substrate and defined by an area of increased mass. An acoustic wave generator positioned adjacent an acoustic wave cavity generates, in a first mode, a first acoustic wave that is sensitive to a first substance and insensitive to a second substance on a surface of the acoustic wave cavity. The acoustic wave generator in a second mode generates a second acoustic wave that is sensitive to the second substance on a surface of the acoustic wave cavity. A controller switches the acoustic wave generator between the first and second modes to detect the presence of the first and/or second substances.

These and other advantages and novel features of the present invention, as well as details of an illustrated embodiment thereof, will be more fully understood from the following description and drawings.

BRIEF DESCRIPTION OF THE SEVERAL VIEWS OF THE DRAWING

FIG. 5 is a side, cross-sectional view of an acoustic wave sensor in accordance with another embodiment of the present invention utilizing a number of electromagnetic acoustic transducers positioned adjacent an acoustic wave cavity for generating a torsional wave that is sensitive to ice and insensitive to water and for generating an acoustic wave that is sensitive to water;

FIG. 6 is a bottom view of the acoustic wave sensor shown in FIG. 5;

FIG. 9 is a flow chart illustrating a foreground process; and

FIGS. 10A–E form a flow chart illustrating a background process.

DETAILED DESCRIPTION OF THE INVENTION

Figure 1:
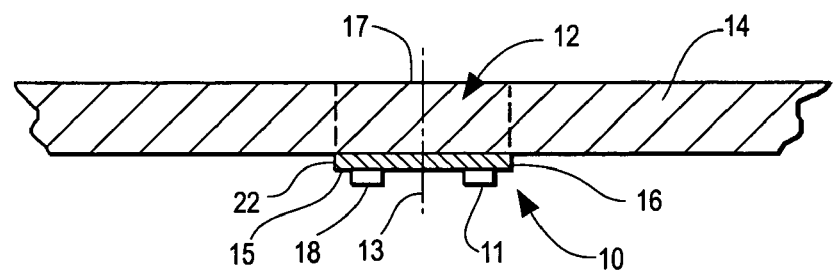
FIG. 1 is a side, cross-sectional view of an acoustic wave sensor of the present invention with one transducer for generating a torsional acoustic wave trapped in an acoustic wave cavity for detecting ice and with a second transducer for generating an acoustic wave sensitive to water for detecting the presence of water on a surface of the cavity.

An acoustic wave sensor 10, in accordance with the present invention as shown in FIGS. 1–6, includes a transducer 11, 11' positioned adjacent an acoustic wave cavity 12 such that the transducer 11, 11' is off-center with respect to the centerline 13 of the cavity 12 to generate a trapped or resonant torsional acoustic wave in the acoustic wave cavity 12. The acoustic wave cavity 12 is formed in a noncylindrical substrate 14 wherein the transducer 11, 11' generating the trapped torsional acoustic wave is in a plane that is parallel to a planar surface 15 of the acoustic wave cavity 12. Because torsional waves can be trapped in a cylindrical substrate, the acoustic wave cavity of the sensor 10 can also be formed in a cylindrical substrate. It has been found that a trapped, torsional acoustic wave generated in accordance with the present invention is sensitive to a first substance such as ice contacting a surface 17 of the acoustic wave cavity but is insensitive to water. That is, an acoustic wave ice detector or sensor, for example, utilizing a trapped torsional wave generated in accordance with the present invention will not register the presence of ice when only water is present where the water level is a multiple of ½λ, the wavelength of the wave, or in the presence of only water the level of which is varying.

An acoustic wave sensor that detects the presence of ice alone need only have the transducer 11, 11' for generating a trapped torsional acoustic wave; although, as described below, multiple transducers such as the transducers 11' and 19 can be used to generate a trapped torsional wave as well. In order to determine the presence of water on the acoustic wave cavity, a different set of transducers are used to generate a different acoustic wave trapped in the cavity 12 that is sensitive to water. Specifically, the acoustic wave sensor 10, when operating in a first mode, uses a first transducer set formed of the transducer 11 in the embodiment of FIG. 1 and the transducer 11' alone or in combination with transducer 19 in the embodiment of FIG. 5 to generate a trapped torsional acoustic wave that is sensitive to ice and insensitive to water. The acoustic wave sensor 10, when operating in a second mode uses a second transducer set formed of the transducers 11 and 18 for the embodiment of FIG. 1 and the transducer 18' for the embodiment of FIG. 5 to generate a trapped shear wave with flexural or compressional components that are sensitive to water as well as to ice. A signal is provided in the first mode of operation from one or more of the transducers of the first set representing the torsional acoustic wave in the cavity 12. The signal is analyzed in accordance with the circuit of FIG. 7 to determine the presence of ice by comparing a value representing the acoustic wave signal to a reference representing the presence of ice. If the value is less than the ice reference, ice is detected. Similarly, a signal is provided in the second mode of operation from one or more of the transducers of the second set representing the trapped shear wave in the cavity 12. The signal is analyzed by the circuit of FIG. 7 to determine the presence of water on a surface of the acoustic wave cavity by comparing a value representing the acoustic wave signal to a reference representing the presence of water. If the value is less than the water reference, water is detected. If the torsional acoustic wave signal does not indicate a sensed event but the shear acoustic wave signal does indicate a sensed event, then water is detected on the acoustic wave cavity 12, but ice is not detected. If the torsional acoustic wave signal does indicate a sensed event, then ice is detected on the acoustic wave cavity.

The acoustic wave cavity 12 is defined by a raised area 16, 16' the cavity extending through the thickness of the substrate 14 from the surface 15 to the surface 17. The acoustic wave cavity 12 is formed on the substrate 14 by an area of increased mass such that the mass per unit surface area of the cavity 12 is greater than the mass per unit surface area of the substrate 14 immediately adjacent the cavity 12. It is noted, that the acoustic wave cavity can also be defined by an area of increased mass that is not raised above the substrate. Such cavities can be formed, for example, by depositing a thin layer of material on the surface of the substrate in an area defining the acoustic wave cavity. Such cavities can also be formed with materials of greater mass than the substrate throughout the cavity or in a portion thereof.

Figure 3:
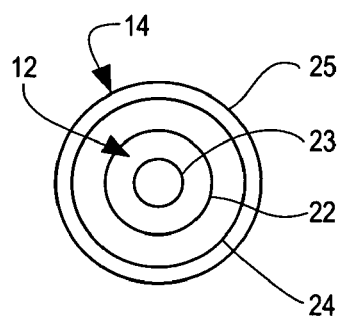
FIG. 3 is a top view of a sensor disk in accordance with another embodiment of the present invention.
Figure 4:
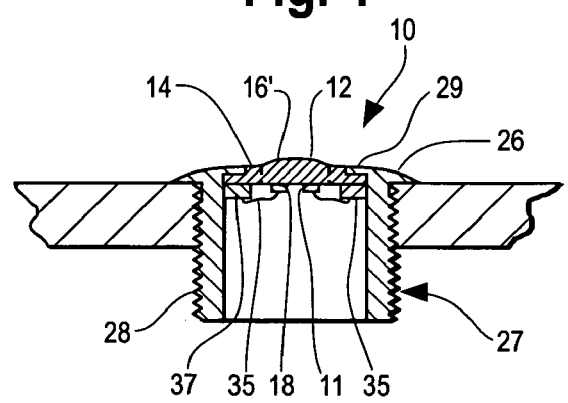
FIG. 4 is a side, cross-sectional view of the sensor disk of FIG. 3 in an individual sensor housing or support.

The raised area defining the acoustic wave cavity may be square, rectangular or other shapes. However, in a preferred embodiment, the raised area has a circular circumference or peripheral edge 22. The raised area 16 may have a flat surface 15 as shown in FIG. 1 or it may have a curved surface such as a dome. In FIGS. 3–5, the acoustic wave cavity 12 is defined by a raised area 16' having the shape of a truncated dome. Although the raised area 16' as shown in FIGS. 4 and 5 is depicted as an integral part of the substrate 14, the raised area may also be formed as a separate piece such as a decal that is bonded to the substrate as depicted by the raised area 16 of FIG. 1. In such an embodiment, the raised area may be formed of the same material as the substrate or of a different material. Moreover, the transducer 11, 11' can be mounted adjacent the raised area 16 as shown in FIG. 1 or the transducer 11, 11' can be positioned adjacent a surface of the acoustic wave cavity opposite the surface of the raised area 16' of the cavity 12 as shown in FIGS. 4 and 5.

The height and geometry of the acoustic wave cavity 12 that will support a trapped or resonant torsional acoustic wave is the same as the height and geometry requirements of an acoustic wave cavity supporting a trapped shear wave as described in U.S. patent application Ser. No. 09/998,355, filed Nov. 20, 2001 and incorporated herein by reference. As described therein, for a shear wave having a harmonic mode, n greater than or equal to 1, the thickness of the cavity from the surface 15 to the surface 17, $b_c$, should be greater than $\frac{1}{2}\lambda$, where $\lambda$ is the wavelength of the fundamental, zeroth order mode. For shear waves having a harmonic mode of $n \geq 1$, separate cutoff frequencies exist for the acoustic cavity and the adjacent region of the substrate. These cutoff frequencies, designated $f_c$ and $f_s$ respectively, determine the frequency range in which standing waves, and hence resonance, is possible. For wave frequencies below $f_c$, no waves propagate. For wave frequencies between $f_c$ and $f_s$, standing waves can form because of reflections at the acoustic cavity boundaries. At wave frequencies above $f_s$, the waves will not be substantially trapped within the acoustic cavity and will propagate throughout the substrate. Thus, at frequencies above $f_s$, resonance in the acoustic cavity is suppressed due to substantial leakage of acoustic energy into the surrounding areas in the substrate. The cut-off frequencies $f_c$ and $f_s$ are given by the following formulas.

$$f_c = \frac{nV_s}{2b_c} \quad f_s = \frac{nV_c}{2b_s}$$

where $b_c$ is the thickness of the acoustic cavity; $b_s$ is the substrate thickness in the area adjacent the acoustic cavity; $V_s$ is the velocity of the zeroth order mode shear wave in the substrate; $V_c$ is the velocity of the zeroth order mode shear wave in the cavity and n is the order of the harmonic mode of the generated shear.

In a preferred embodiment, the cavity is operated in only a single mode. To accomplish this in practice, the geometry of the acoustic cavity is such that the ratio of the length to thickness of the cavity satisfies the following equation where the length is designated as 2a.

$$\frac{2a}{b_c} \leq \frac{1}{n}\sqrt{\frac{2b_s}{h_c}}$$

where $h_c$ is the height of the raised area defining the cavity such that $h_c = b_c - b_s$. Similarly, the width w, of the acoustic cavity should satisfy the same relationship as follows.

$$\frac{w}{b_c} \leq \frac{1}{n}\sqrt{\frac{2b_s}{h_c}}$$

In order to generate a shear wave with a harmonic mode of 1 or greater that is trapped in such an acoustic wave cavity, a transducer such as the electromagnetic acoustic transducer 18' or a piezoelectric transducer can be centered on the cavity centerline 13. For a cavity 12 having a circular peripheral edge, the length of a piezoelectric transducer should be along a diameter of the acoustic wave cavity. A shear wave can also be generated using two transducers such as transducers 11 and 18 as described below. For an acoustic wave cavity formed as described above, by positioning an acoustic wave transducer 11, 11' such that the center of the transducer is off-center with respect to the centerline 13 of the acoustic wave cavity 12 as described in detail below, a torsional acoustic wave can be generated and trapped in the cavity 12.

For an acoustic wave cavity defined by a raised area having a peripheral edge that is perpendicular to the adjacent surface of the substrate 14 as shown in FIG. 1, the preferred placement of the transducer 11, 11' for generating a trapped torsional wave is at a distance from the cavity centerline 13 of 0.8 times the radius R of the acoustic wave cavity 12.

Figure 2:
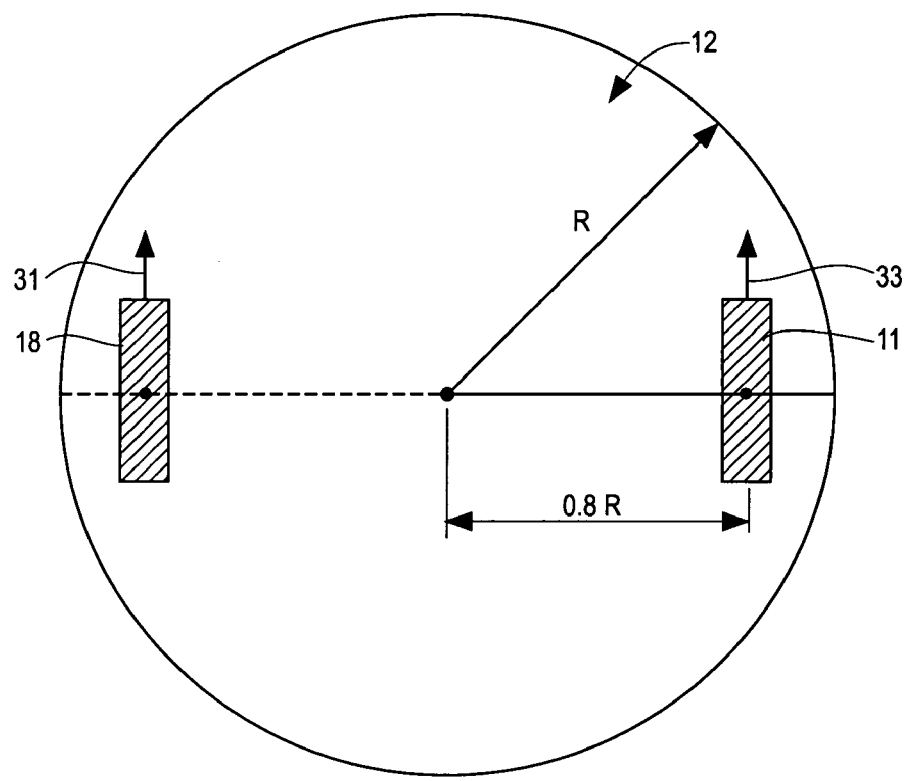
FIG. 2 is a bottom view of the acoustic wave cavity of the sensor shown in FIG. 1.

More particularly, as shown in FIG. 2, the transducer 11, which in this embodiment is a piezoelectric transducer, is mounted on the acoustic wave cavity 12 such that the center of the transducer is located on a radius of the cavity at a distance from the centerline 13 that is 0.8 times the radius R of the acoustic wave cavity 12 with the length of the transducer 11 extending at a right angle with respect to the radius of the acoustic wave cavity 12. It is noted that, for an acoustic wave cavity having a peripheral edge that is not perpendicular to the adjacent surface of the substrate, such as the peripheral edge of a dome shaped raised area, the placement of the center of the transducer 11, 11' is preferably at a distance from the centerline 13 of 0.6 times the radius R of the acoustic wave cavity. It should be appreciated that the distance of the center of the transducer 11, 11' from the centerline 13 can be outside of the range 0.6 R to 0.8 R and still generate a torsional acoustic wave. The range of 0.6 R to 0.8 R has been found to be the preferred distance from the cavity centerline for an acoustic wave cavity described above.

In order to generate a trapped shear wave using a single piezoelectric transducer, the transducer is preferably centered on the centerline 13 of the cavity. In an alternative embodiment shown in FIGS. 1 and 2, both the transducers 11 and 18 are used to generate the trapped shear wave wherein the polarity of the transducer 18, as depicted by the arrow 31, is in the same direction as the polarity of the transducer 11 depicted by the arrow 33 and the centers of the transducers 11 and 18 are positioned on a diameter of the acoustic wave cavity on opposite sides of the centerline 13. Further, the centers of the transducers 11 and 18 are located at a distance from the centerline 13 of 0.8 times the radius R of the acoustic wave cavity in this example. Again, the length of each of the transducers 11 and 18 is at an angle with respect to the diameter of the acoustic wave cavity, the angle preferably being 90°. Because the polarity 31 of the transducer 18 is in the same direction as the polarity 33 of the transducer 11, when both transducers are driven, a shear wave having flexural and or compressional components is generated and trapped in the acoustic wave cavity 12. By driving the transducer 11 alone, a torsional wave is generated and trapped in the acoustic wave cavity 12 to detect the presence of, for example, ice, on a surface 17 of the acoustic wave cavity 12. The torsional wave, however, is insensitive to water on the surface 17. If it is desired to determine the presence of water alone or water and ice on the surface 17 of the acoustic wave cavity 12, both of the transducers 11 and 18 are driven so as to generate a shear wave with flexural and/or compressional components wherein the wave is trapped in the acoustic wave cavity 12.

Although the presence of a torsional acoustic wave trapped in an acoustic wave cavity and the presence of a transverse shear acoustic wave trapped in an acoustic wave cavity can be determined by a number of different methods, one method is as follows. First, it should be appreciated that trapped acoustic wave modes are standing waves and standing waves have nodes and antinodes. One way to detect the position of a node on an acoustic wave cavity is to slide a pointed acoustic wave absorbing stylus, such as a toothpick, across the acoustic wave cavity surface 17 and to look at the impedance peak of the signal representing the acoustic wave energy trapped in the cavity where the signal is provided by the transducer 11, 11'. When the stylus is over a node, that is, over a place of maximum amplitude, maximum absorption of the acoustic wave by the stylus is obtained and the impedance peak dips. By moving the stylus across the surface 17 of the acoustic wave cavity and marking the spots where maximum acoustic wave absorption occurs, an image or map of nodal lines can be obtained. For a torsional wave trapped in the acoustic wave cavity, the nodal lines are circles. The circular nodal lines are typically centered on the acoustic wave cavity 12. This is opposed to the nodal lines that are obtained when a shear wave is generated as by a center bonded piezoelectric transducer. For such a shear wave, the nodal lines are linear and extend parallel to the length of the transducer.

The ice detector or ice and water detector depicted in FIGS. 1 and 2 can be readily incorporated into any structure without modifying the structure itself by bonding a decal forming the raised area 16 onto a surface of the structure so as to form an acoustic wave cavity 12 therein and by adding one or more transducers 11 and 18 on a surface 15 of the cavity opposite the active surface i.e., substance responsive surface 17. Such structures can be the outer material of an airplane wing, or a refrigerator or freezer wall, etc. For applications where it is desired to have ready access to the acoustic wave sensor from a side of the structure adjacent the active surface 17, the sensor 10 is contained in a sensor support 27 such as shown in FIG. 4. The sensor support 27 has a head portion 26 containing the acoustic wave cavity 12 and a cylindrical body with threads 28 (or no threads if desired). The support 27 forms an insert so that the sensor 10 can be mounted in an aperture of the structure on which it is desired to detect ice and/or water. The sensor 10 in the support 27 can be inserted and removed from the external or active side of the sensor for easy maintenance.

In a preferred embodiment, the acoustic wave cavity 12 is formed in a substrate 14 that is itself an insert as shown in FIG. 3, wherein the substrate insert is mounted in an aperture of the sensor support 27. The substrate insert 14 of FIGS. 3 and 4 is a stamped disk, herein after referred to as the sensor disk. The sensor disk is formed with a raised area 16' that defines an acoustic wave cavity 12 as discussed above. Because the disk is a stamped piece of material, the sensor disk can be manufactured very cheaply. In a preferred embodiment, the raised area 16' has the shape of a truncated dome with an outer circular periphery 22 with a diameter of, for example, 0.30 inch. The diameter of the periphery 23 of the truncated portion of the dome can vary. The periphery 24 of the sensor disk insert is spaced from the periphery 22 of the acoustic wave cavity. A preferred diameter of the periphery 24 is, for example. 0.50 inch. The sensor disk periphery 24 also includes a flange 25 extending thereabout so as to engage a corresponding flange 29 of the sensor support 27. The diameter of the flange may be, for example, 0.58 inch. The sensor disk may be very thin such as on the order of 0.065 inch where the height of the raised area 16' is as discussed above. As shown in FIG. 4, the sensor disk 14 is mounted in an aperture of the structure on which ice is to be detected wherein the body 28 extends through the aperture. The head portion 26 can be similar to the head of a bolt or the like, but contoured as discussed above to form an acoustic wave cavity. As such, the sensor 10 of FIG. 4 can be easily removed from an external side of the structure.

In a preferred embodiment, the body of the support 27 is hollow so that contacts, such as the contacts 35 for the transducers 11 and 18 can be disposed therein. As shown, the contacts 35 are mounted on a circuit board washer 37. The circuit board washer 37 is annular in shape, having an aperture aligned with the acoustic wave cavity 14. The washer is bonded to a peripheral portion of a back surface of the sensor disk spaced from the acoustic wave cavity 14 and to a back or inner portion of the head 26 of the support 27.

The circuit board washer 37 provides a connection from the contacts 35, and thus the transducers 11, 18 to pins or a connector carried on the washer where the washer pins/connector is coupled to leads extending through the hollow portion of the support 27 and to a remote circuit board via the leads. Alternatively, the washer pins/connector provide a direct connection to a circuit board that is mounted in the hollow portion of the support 27. It is noted, that the sensor disk can be formed of any material capable of supporting a trapped or resonant acoustic wave such as a metal, ceramic, etc. The support 27 may be formed of any material desired for the application for which the sensor is to be used.

As shown in FIGS. 5 and 6, the transducers 11' and 18' are electromagnetic transducers that include one or more magnets 20 and a coil 41 for the transducer 11' and a coil 43 for the transducer 18'. The electromagnetic transducer 18' has its coil 43 centered on the centerline 13 of the acoustic wave cavity 12. When the transducer 18' is driven alone, by current flowing through the coil 43, the transducer 18' generates a shear wave that is trapped in the acoustic wave cavity 12. As discussed above, the shear wave includes flexural components that are sensitive to both ice and water whereas the trapped torsional wave generated by the transducer 11' alone or by the transducers 11' and 19 together is sensitive to ice but is insensitive to water. As noted, the transducer 11', alone, can generate a torsional acoustic wave in the cavity 12 for detecting ice. Alternatively, the transducer 11' can be used in combination with an electromagnetic transducer 19 having a coil 45 for generating a torsional wave in the acoustic wave cavity 12. When multiple transducers such as the transducer 11 and 19 are driven together to generate a torsional acoustic wave, the current flowing through the coil 19 should be in a direction opposite to the direction of current flow in the coil 11 where coils 11' and 19 are located on a diameter of the cavity 12 on opposite sides of the centerline 13. Because the raised area 16' has a peripheral edge that is not perpendicular to the adjacent surface of the substrate 14, the centers of the coils 41 and 45 are at a preferred distance from the centerline 13 of 0.6 times the radius R of the acoustic wave cavity 12. It should be appreciated that, if the raised area defining the acoustic wave cavity has a peripheral edge that is perpendicular to the adjacent surface of the substrate 14, then the centers of the coils 41 and 45 are preferably at a distance from the centerline 13 of 0.8 times the radius R of the acoustic wave cavity. In a preferred embodiment, the coils 41, 43 and 45 lie in a plane which is parallel to a planar surface 15 of the acoustic wave cavity 12. As noted above, the transducers may be positioned adjacent either the planar surface 15 or the non-planar surface 17 of the raised area 16'. FIG. 6 also illustrates the positioning of a pair of magnets 20 and 22 underneath the coils 41, 43 and 45 and the acoustic wave cavity 12. The magnets 20 and 21 are positioned with the North pole of the magnet 20 adjacent the South pole of the magnet 21. As used herein, the center of an electromagnetic acoustic wave transducer is the center of the coil. Further, a single electromagnetic acoustic transducer will have a single coil, whereas multiple electro-magnetic acoustic wave transducers have multiple coils but may share one or more magnets. That is, the number of transducers is equal to the number of coils.

Figure 7:
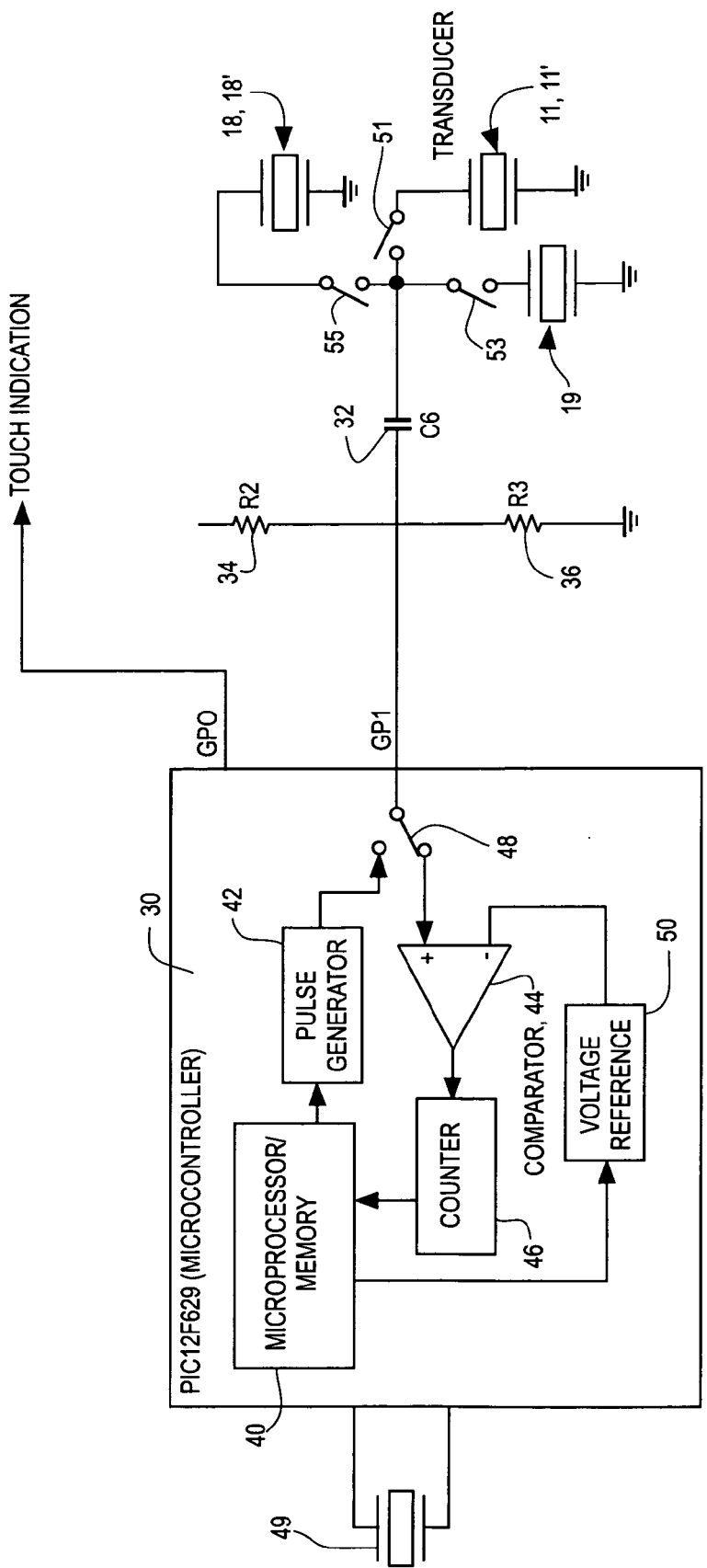
FIG. 7 is a block diagram illustrating a detection circuit of the present invention.

A circuit for detecting a sensed event such as the presence of a first substance such as ice and the presence of a second substance such as water is shown in FIG. 7. The circuit includes a controller 30 that is coupled to the acoustic wave transducers 11, 18 for the embodiments of FIGS. 1–4 or to the transducers 11', 18' and 19 for the embodiments of FIGS. 5 and 6. The controller, in the first mode of operation and in a first portion of a sampling cycle, drives the first set of transducers to generate a torsional acoustic wave in the cavity 12. For the FIG. 1 embodiment, the controller 30, in the first mode of operation, closes the switch 51 and opens switches 53 and 55 to drive the transducer 11 to generate a torsional wave. For the FIG. 5 embodiment, the controller 30, in the first mode of operation closes the switches 51 and 53 and opens the switch 55 to drive the transducers 11' and 19 to generate a torisonal acoustic wave. The controller 30, in a second mode of operation, closes the switches 51 and 55 and opens the switch 53 for the FIG. 1 embodiment to generate a trapped shear wave with transducers 11 and 18 or the controller 30 closes switch 55 and opens switches 51 and 53 for the FIG. 5 embodiment to generate a trapped shear wave with the transducer 18'. A capacitor 32 is connected between the transducers and a pair of resistors 34 and 36 wherein the resistors set the D.C. level of the transducer signal.

The controller 30, in each of the first and second modes of operation, drives the respective transducers to generate the desired acoustic wave in the cavity 12 in a first portion of a sampling cycle as discussed above. In a second portion of the sampling cycle, the controller 30 is responsive to the signal from one or more of the transducers representing the acoustic wave in the acoustic wave cavity to analyze the signal for a sensed event. In a preferred embodiment, in the first mode of operation, the controller 30 closes the switch 51 and opens switches 53 and 55 to pick up the torsional acoustic wave signal from the transducer 11, 11' in the second portion of the sampling cycle. Further, in the second mode, the controller 30 closes the switch 55 and opens switches 51 and 53 to pick up the shear acoustic wave signal from the transducers 18, 18' in the second portion of the sampling cycle. The sensed event, as described above, can be the presence of ice and/or water in one embodiment of the present invention. The sensed event can also be the presence of other substances as well. The circuit of FIG. 10 will be described below for sensing or detecting contact of a substance or a touch by a substance on the active or responsive surface 17 of the acoustic wave cavity 12. As used herein, a "touch" on the acoustic wave cavity refers to contact of a substance on the cavity 12 where the acoustic wave is sensitive to the substance in the current, active mode such as contact by ice in the first mode or contact by water in the second mode.

The controller 30 may be a PIC12F629 microcontroller that includes a microprocessor 40 with associated memory, a pulse generator 42, a comparator 44 and a timer or counter 46. An oscillator 49 provides a clock input to the controller, timers, etc. The controller 30 also includes a switch 48 that is controlled by the microprocessor 40 to switch line Gp1 from an output line in the first portion of the sampling cycle to an input line in the second portion of the sampling cycle. More particularly, in the first portion of the sampling cycle, the switch 48 couples the line Gp1 to the pulse generator 42 so that under the control of the microprocessor 40, the pulse generator 42 outputs one or more pulses to the transducer(s) to be driven for the active mode to generate a resonant acoustic wave in the acoustic wave cavity 12. In the second portion of the sampling cycle, the microprocessor 40 controls the switch 48 to couple the line Gp1 to the comparator 44 so that the signal from the transducer 11, 11' or 18, 18' depending on the active mode and representing the acoustic wave in the acoustic wave cavity will be coupled to the comparator 44.

The selected transducers for the active mode may be driven by one pulse from the controller 30 in the first portion of the sampling cycle. Alternatively, the transducer may be driven by multiple pulses, in which case the pulse frequency should be within ten to fifteen percent of the resonant frequency of the cavity 12. Preferably, the pulse frequency is within plus or minus five percent of the cavity's resonant frequency. When the transducer set for the active mode is driven by one or several drive pulses to generate a resonant acoustic wave in the cavity 12, after the drive pulses cease to be applied to the transducer, the acoustic wave continues to resonate in the cavity but the amplitude of the wave gradually decreases over time. The voltage across the transducer 11, 11' or 18, 18' representing the acoustic wave in the presence of a substance to which the acoustic wave is sensitive decays to a predetermined level in a shorter period of time than the acoustic wave in a cavity that is not contacted by a substance to which the acoustic wave in the cavity is sensitive to. The controller 30, as discussed below, determines a value representing the period of time that the acoustic wave signal for a sampling cycle decays to a predetermined level. The controller 30, when operating in the first mode, compares the determined value for a sampling cycle to an ice reference to detect the presence of ice on the acoustic wave cavity during the sampling cycle. The controller 30, when operating in the second mode, compares the determined value for a sampling cycle to a water reference to detect the presence of water on the acoustic wave cavity during the sampling cycle. In one embodiment of the present invention as discussed below, the value representing the period of time that the acoustic wave signal decays to a predetermined level is the number of cycles of the acoustic wave signal, during a given scan count time of a sampling cycle, having an amplitude above a predetermined level.

More particularly, during the second portion of the sampling cycle, the acoustic wave signal from one or more of the transducers active for the given mode is coupled by the switch 48 to one input of the comparator 44. The comparator compares the acoustic wave signal to a predetermined reference voltage input to a second input of the comparator 44 by the microprocessor/memory 40. Preferably, the reference voltage 50 is a programmable value. The output of the comparator goes high when the acoustic wave signal is above the reference signal and the output of the comparator goes low when the acoustic wave signal falls below the reference signal. Because the acoustic wave signal is cyclical, the comparator generates an output pulse for each cycle of the acoustic wave that is greater than the predetermined reference. The output of the comparator 44 is coupled to a counter 46 that counts the number of pulses generated during a scan count time as discussed in detail below. The number of pulses, representing the period of time that the acoustic wave signal decays to a predetermined level represented by the reference signal 50, is applied to the microprocessor 40. The microprocessor 40 is responsive to the number output from the counter 46 to compare that number to a second reference representing a sensed event, i.e. ice contact or water contact depending on the active mode in order to sense or detect the event.

Figure 8A:
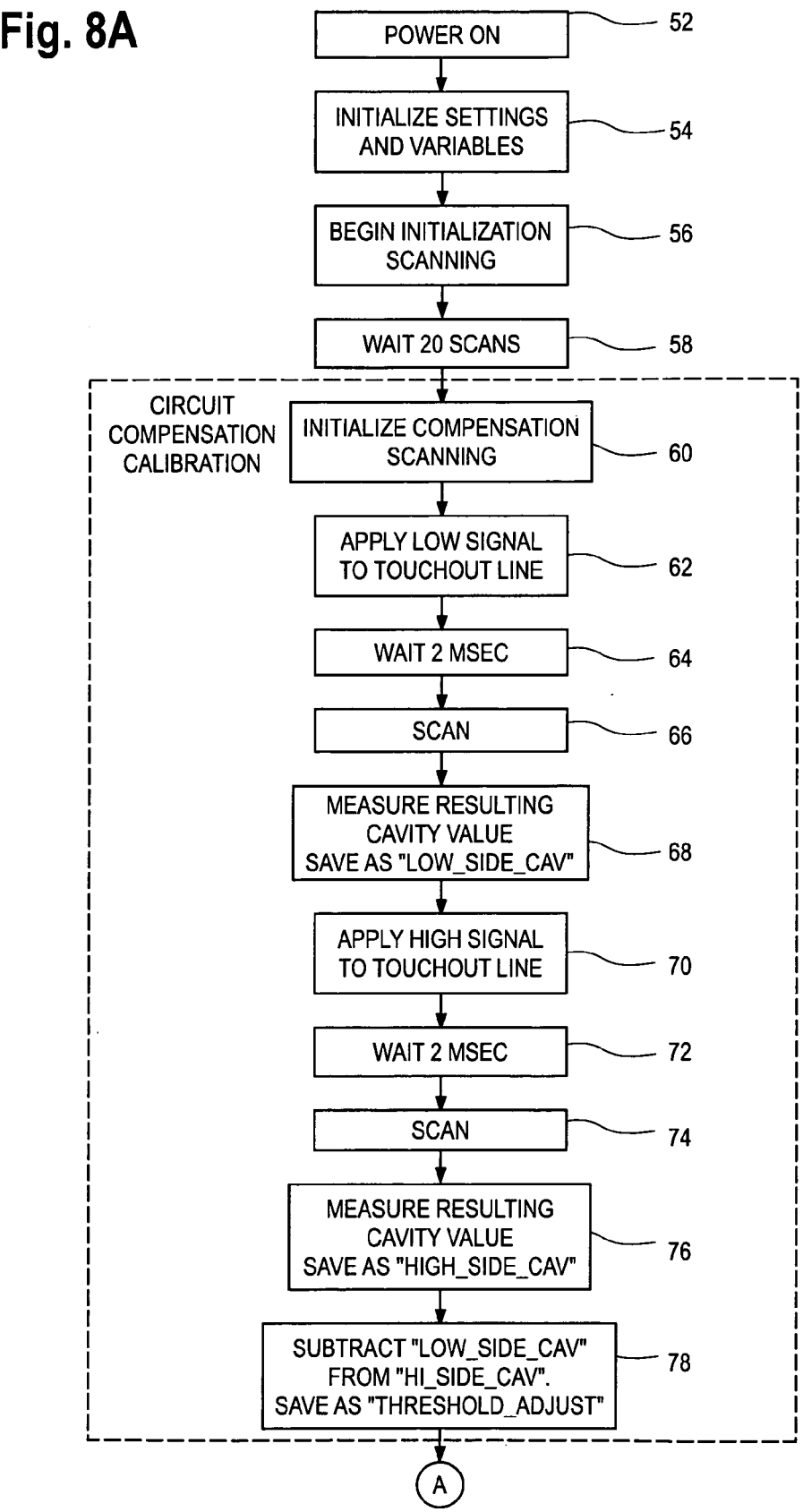
FIGS. 8A–B form a flow chart illustrating a routine for initializing and starting a scan or sampling cycle.
Figure 8B:
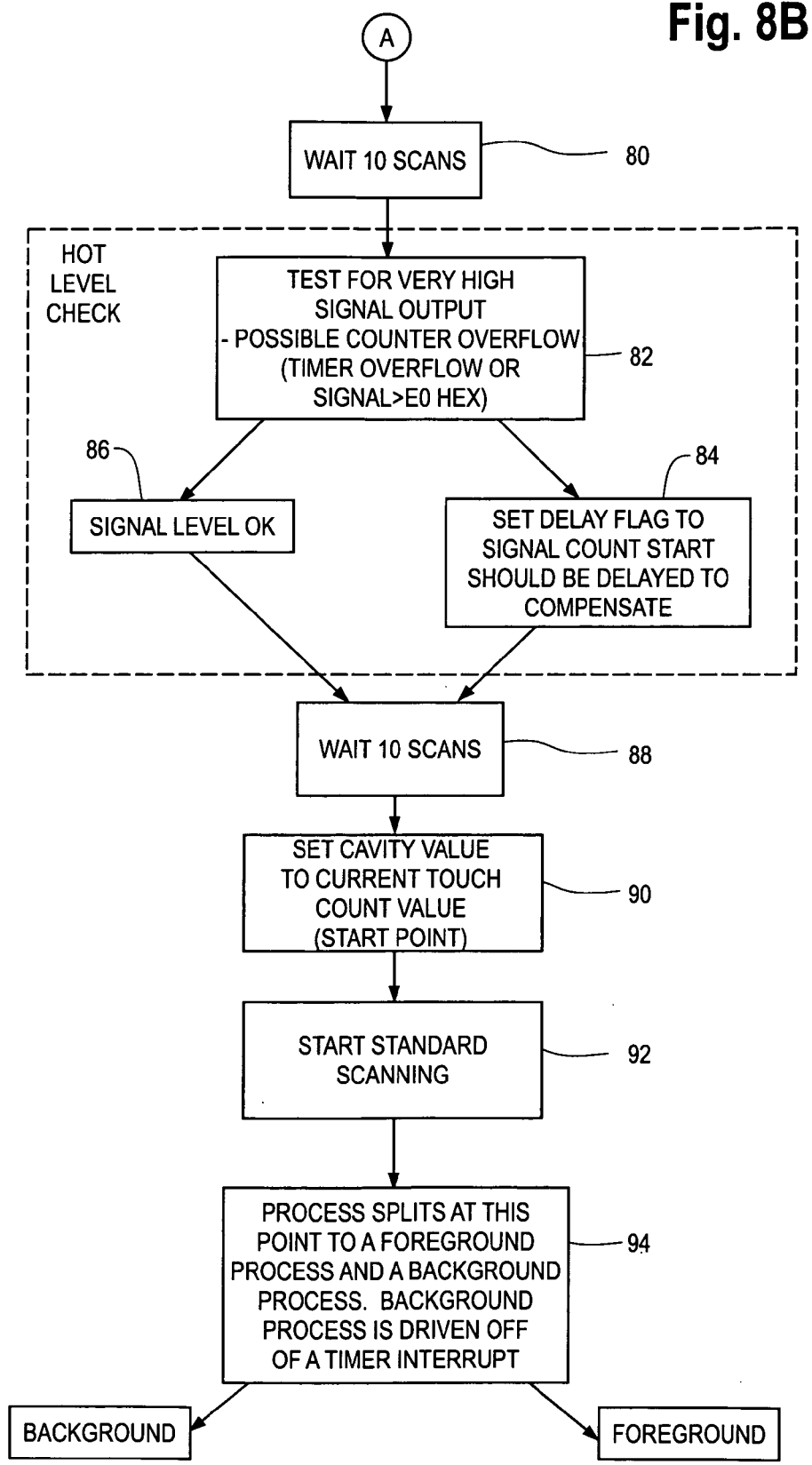
Figure 10B:
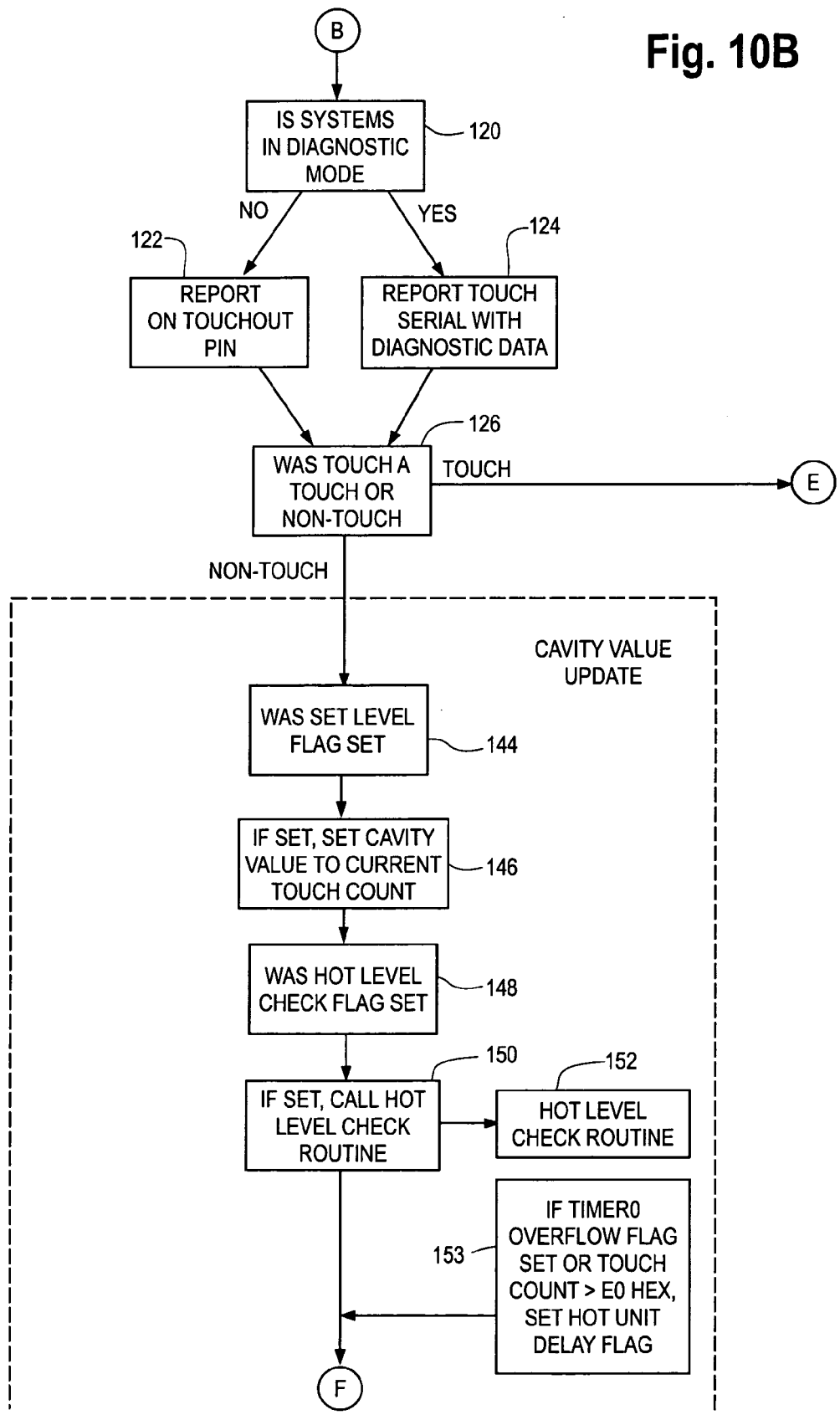
Figure 10C:
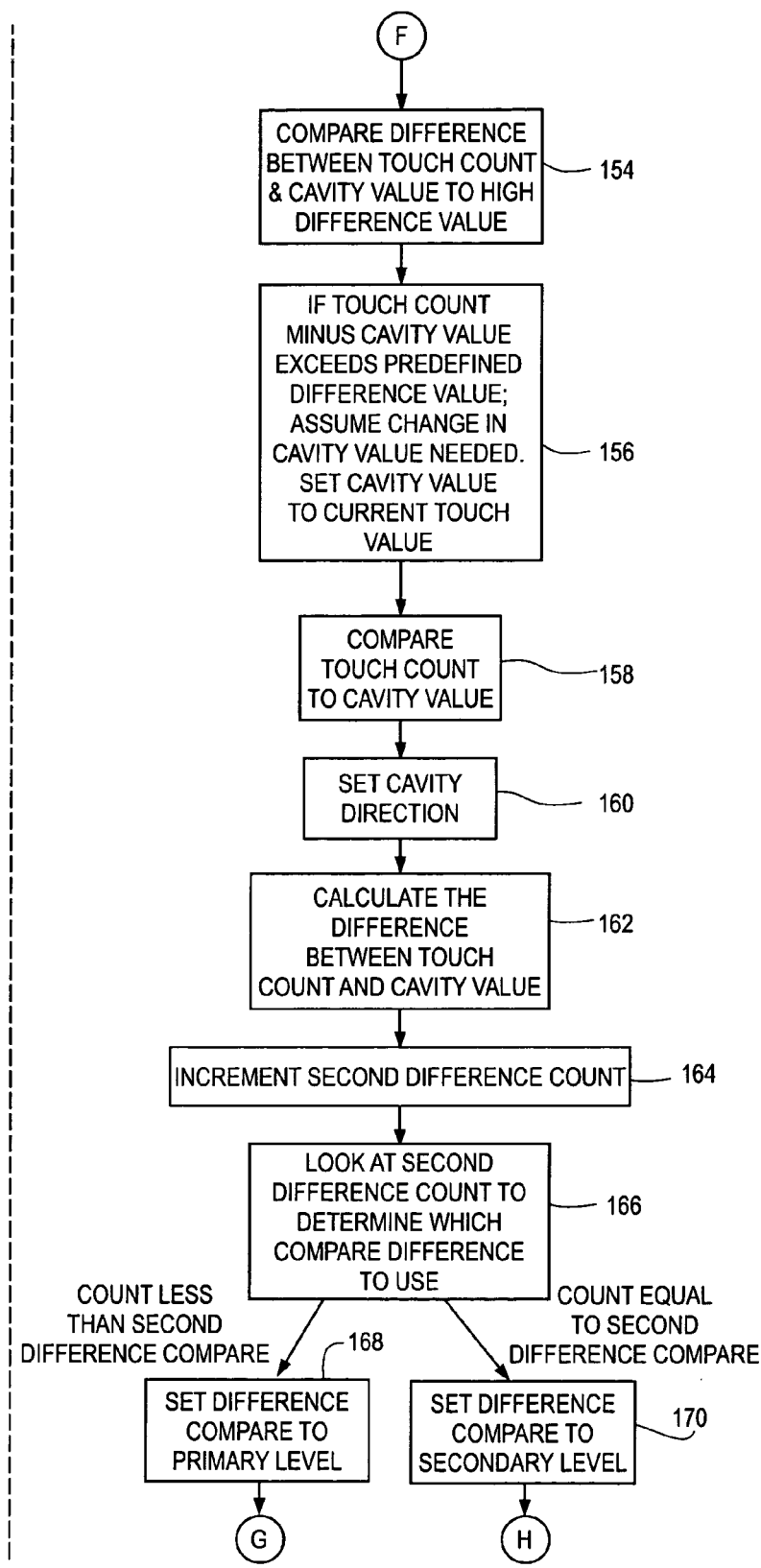
Figure 10D:
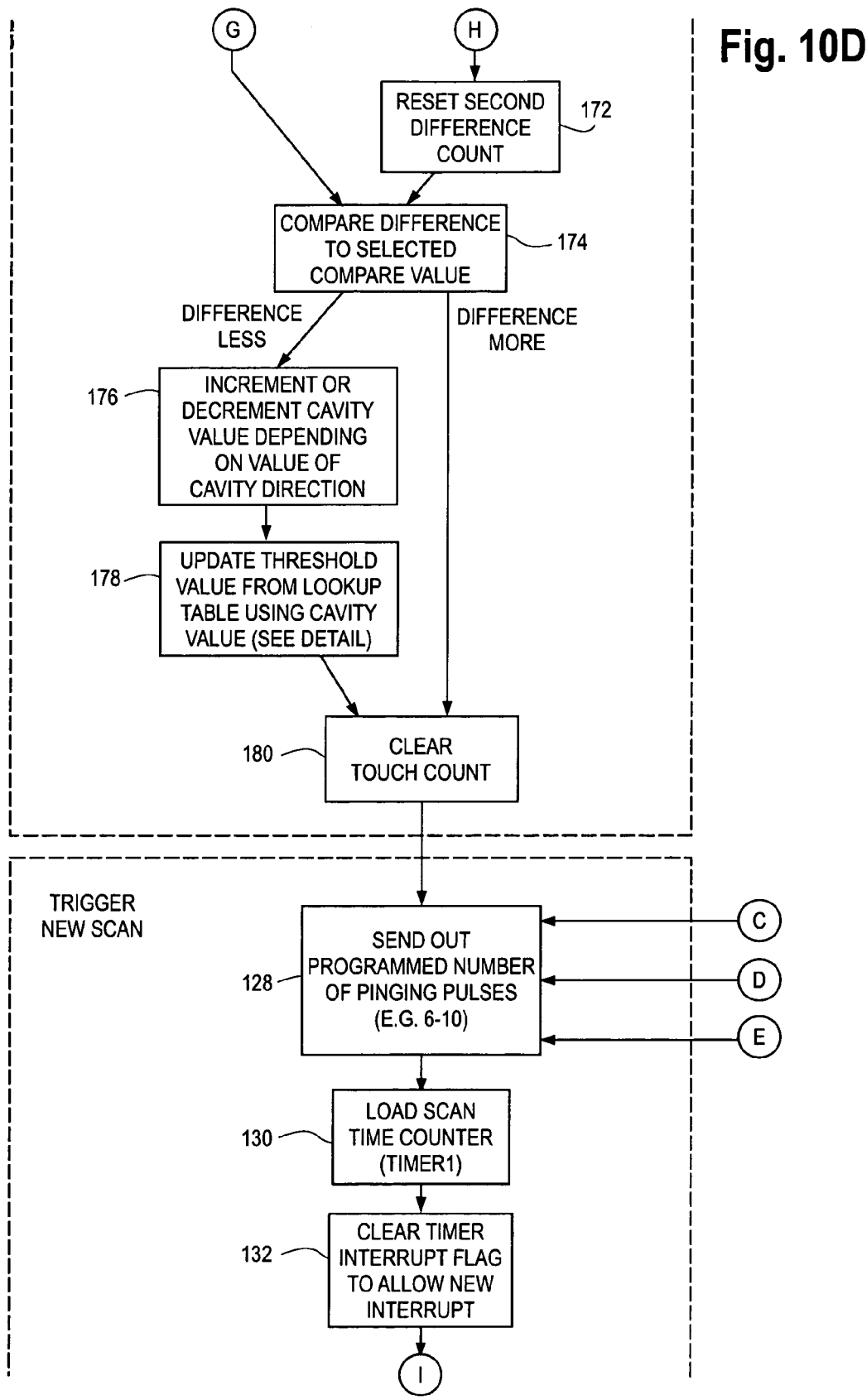
Figure 10E:
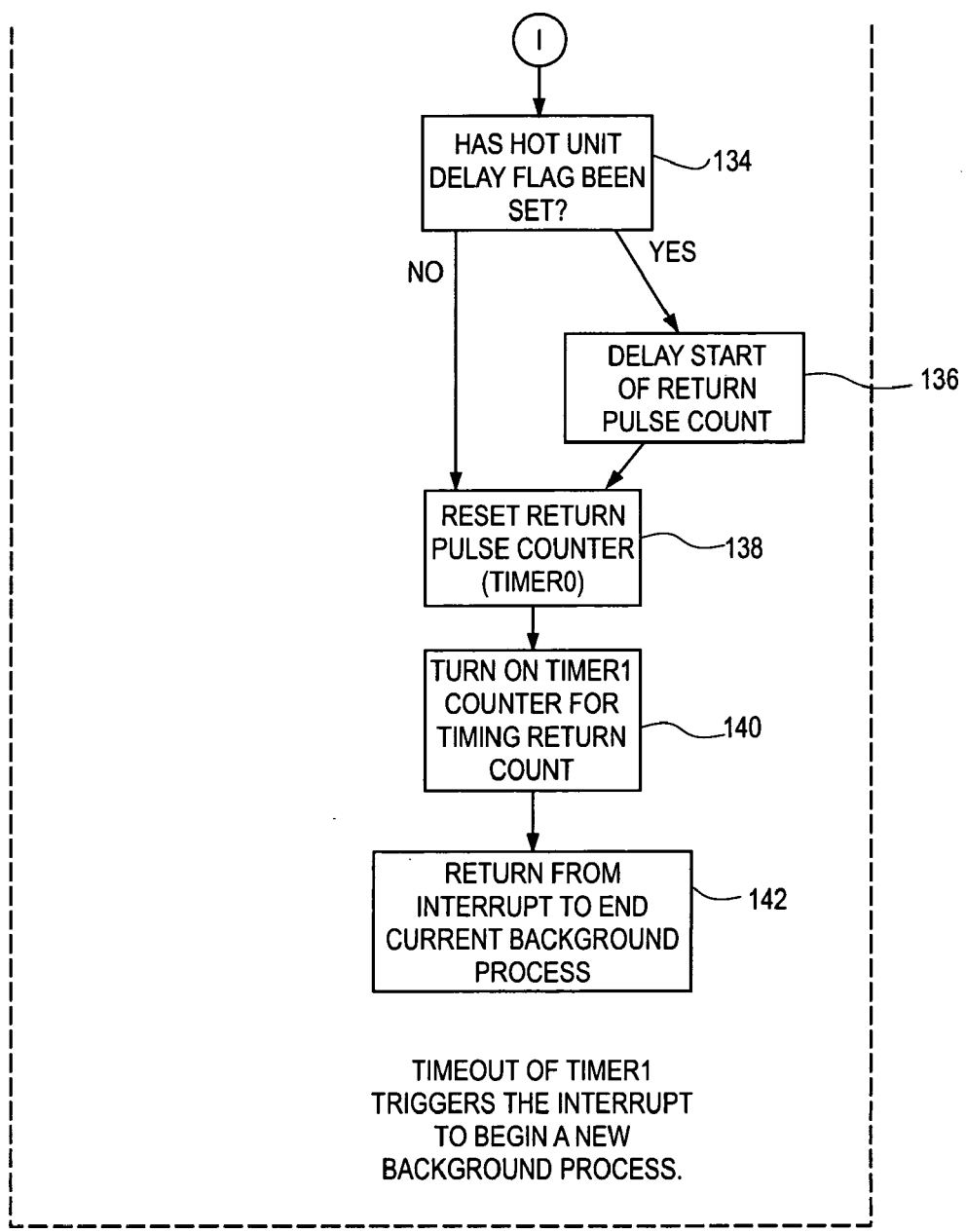

The microprocessor 40 operates in accordance with the flow charts depicted in FIGS. 8A–B, 9 and 10A–E. As shown in FIG. 8A, when the detection circuit 10 is powered on, as determined at block 52, the microprocessor at block 54 initializes various settings and variables including the active mode, i.e. either the first or the second mode. Thereafter, at block 56, the microprocessor begins the initialization scanning. During this initialization scanning, six to ten pulses are coupled to the transducer set for the active during a scan, i.e. a sampling cycle, to drive the transducer set to generate the selected resonant acoustic wave in the acoustic wave cavity. Although the active transducers generate a signal representing the acoustic wave in each of the scans or sampling cycles, during the initialization scanning process, the microprocessor does not analyze the acoustic wave signal. The initialization scanning which proceeds over approximately 20 scans as depicted at block 58 allows the system to stabilize when power is first turned on. It is noted that each scan, i.e. sampling cycle, is extremely short being on the order of 300 microseconds to 4 milliseconds so that the time that it takes to perform the 20 scans of the initialization scanning is a negligible period of time. After completing the initialization scanning process, the microprocessor proceeds from block 58 to block 60 to begin a circuit compensation calibration routine.

The circuit compensation calibration routine compensates for current leakage in the circuit 10. This is an optional routine and may not be needed. At block 60, the microprocessor initializes the compensation scanning by setting a flag that indicates that the compensation calibration routine is in effect. At block 62, the microprocessor applies a low signal to the output line Gp0 shown in FIG. 1. After waiting 2 msec at block 64, the microprocessor at block 66 initiates a scan or sampling period by applying six to ten pulses to the active transducer set. At block 68, the microprocessor switches to the second portion of the scan or sampling cycle and measures the resulting count from the counter 46. This count value is saved as a "low_side_cav" value. Thereafter, at block 70, the microprocessor applies a high signal to the output Gp0 of the controller 30. After waiting to 2 msec at block 72, the microprocessor at block 74 again initiates a scan or sampling cycle by driving the transducer 12 with six to ten pulses. At block 76, the microprocessor moves the switch 48 so that the acoustic wave signal from the active transducer is coupled to the comparator 44 and the microprocessor 40 saves the resulting count from the counter 46 as a "high_side_cav" value. At block 78, the microprocessor subtracts "low_side_cav" from "high_side_cav." The resulting difference is saved as "threshold_adjust." From block 78, the microprocessor proceeds to block 80 and initiates ten scans to isolate one process from another. After the ten scans have been completed at block 80, the microprocessor 40 proceeds to block 82 to start a hot level check.

The hot level check is a check for an extremely sensitive acoustic wave cavity that produces a large number of acoustic wave signal cycles above the predetermined reference value 50 when a transducer set is driven by one or more of the drive pulses. At block 82, the microprocessor checks for a very high signal output indicated by an overflow of the counter 46 or a count that is greater than E0 Hex. If the value of the counter 46 indicates a very high signal output, the microprocessor proceeds from block 82 to block 84 to set a delay flag. The delay flag signals the microprocessor that the count should be delayed for a predetermined period of time to compensate for the high signal output. This delay may be accomplished by delaying the moving of the switch 48 from the pulse generator 42 to the comparator 44 so as to reduce the number of pulses output from the comparator 44 to the counter 46 for a very sensitive acoustic wave cavity so that the counter 46 does not overflow. The delay can also be accomplished by delaying the resetting of the counter 46 wherein the counter 46 does not start counting until the counter is reset. If the microprocessor determines at block 82 that the signal output is not too high, the microprocessor proceeds to block 86 indicating that the signal level does not need to be compensated for. From blocks 84 or 86, the microprocessor proceeds to block 88 to initiate ten scans before beginning the next process.

At block 90, the microprocessor 40 sets a "cavity value" to the current "touch count." The "cavity value" represents a running average of non-contacted state and is calculated as described below. The "touch count" is the count from the counter 46 generated during the scan count time for one sampling cycle or scan. At block 92, the microprocessor then begins the standard scanning, i.e. sampling cycle. In particular, at block 92, the microprocessor 40 controls the pulse generator 42 to provide, for example, six to ten pulses to the active transducer set so as to drive the transducer set to generate an acoustic wave in the acoustic wave cavity for one sampling cycle. At block 94, the software or firmware splits into a foreground process and a background process. The foreground process as depicted in FIG. 9 is continuously running but is interrupted by a timer interrupt that causes the background process depicted in FIGS. 10A–E to be implemented.

As shown in FIG. 9, the foreground process or routine begins at block 96. At block 96, the microprocessor 40 looks for a request for recalibration. If a request for recalibration flag has not been set, the microprocessor 96 loops back to again monitor for a request. When a request has been posted, the microprocessor proceeds from block 96 to block 98 to shut down the normal scanning operation which began at block 92. Thereafter, at block 99, the microprocessor re-implements the circuit calibration routine depicted in FIG. 8A at blocks 60–78. After finishing the circuit calibration routine, the microprocessor proceeds to block 92 to resume the standard scanning operation.

The background process or routine depicted in FIGS. 10A–E starts when a timer 1 interrupt is generated. The timer 1 interrupt is generated at the end of the scan count time for a given sampling cycle. At block 100, the microprocessor 40 saves the "touch count" which, again, is the number of pulses counted by the counter 46 for a given scan, i.e. sampling cycle during the scan count time. At block 102, the microprocessor 40 determines whether the counter 46 has overflowed and if so, the microprocessor 40 sets the hot level check flag. This is a re-check for the hot level to again enable a highly sensitive acoustic wave cavity to be compensated for. Thereafter, at block 104, the microprocessor looks at the previous output on line Gp0. If the previous output was a 1 indicating a sensed event, the microprocessor 40 adds the "threshold_adjust" value determined at block 78 to the current threshold. It is noted, that if no adjustment is needed, the value of "threshold_adjust" will be zero. At block 106, the microprocessor 40 determines whether the "touch count" saved at block 100 is less than the current threshold. The current threshold is used as a sensed event reference. The current threshold may be a fixed value but in a preferred embodiment, it is a determined value to compensate for drift or other changes. If the "touch count" value is less than the threshold, i.e. sensed event reference, as determined at block 106, the microprocessor at block 110 sets a "touch current" flag to 1. If the "touch count" value is not less than the threshold as determined at block 106, the microprocessor 40 at block 108 sets the "touch current" flag to 0. Thereafter, the microprocessor proceeds from blocks 108 and 110 to block 112.

At blocks 112, 114 and 118, the microprocessor 40 determines whether the "touch count" values for ten consecutive scans or sampling periods have indicated a sensed event or not. The microprocessor 40 looks for ten consecutive sensed event indications before registering a sensed event so as to prevent a sensed event from being indicated on the output Gp0 as a result of a transient contact with an acoustic wave cavity. Similarly, the microprocessor 40 looks for ten no sensed event indications before registering a no sensed event condition on Gp0 for stability of the detection process. More particularly, at block 112, the microprocessor 40 determines whether the "touch current" value set at either blocks 108 or 110 matches the "touch current" value from the previous scan. If so, the microprocessor 40 proceeds from block 112 to block 114 to increment a touch current count value. Thereafter, at block 118, the microprocessor 40 determines whether a touch current count matches a touch hysteresis value. The touch hysteresis value represents the number of consecutive touch values that must be detected at block 108 before an actual sensed event is reported on the output Gp0. In this example, the touch hysteresis value is set equal to ten. If the touch current value does not match the previous touch current value as determined at block 112, the microprocessor proceeds to block 116 to reset the touch current count. From block 116, the microprocessor proceeds to block 128 to trigger a new sampling cycle, i.e. new scan, by sending out the preprogrammed number of pulses to drive the transducer set for the active mode. Similarly, if the touch hysteresis value has not been met as determined at block 118, the microprocessor 40 proceeds to block 128 to trigger a new sampling cycle.

When the touch hysteresis value has been met indicating ten consecutive sensed events or ten consecutive no sensed event detections at blocks 108 and 110, the microprocessor proceeds from block 118 to block 120. At block 120, the microprocessor 40 determines whether the system is in the diagnostic mode and if so, the microprocessor proceeds to block 124 to report various diagnostic data as discussed in detail below. If the system is not in the diagnostic mode, the microprocessor 40 proceeds from block 120 to block 122. At block 122, the microprocessor 40 provides either a sensed event or a no sensed event signal on Gp0 based on whether the ten consecutive scans indicated a sensed event or no sensed event condition. At block 122, the microprocessor also changes the active mode so that if the sensor was operating in the first mode and, for example an event was sensed indicating the presence of ice for ten consecutive scans, the microprocessor at block 122 changes the mode to the second mode to detect the presence of water. Similarly, if the sensor was in the second mode, at block 122, the microprocessor switches the active mode to the first mode. From blocks 122 or 124, the microprocessor 40 proceeds to block 126 to determine whether the report was of a sensed event or a no sensed event condition. If a sensed event was reported, the microprocessor 40 proceeds from block 126 to block 128. If the condition reported was a no sensed event condition, the microprocessor proceeds to block 144 to begin a process for updating the "cavity value" which represents a running average touch count value for an untouched acoustic wave cavity. As discussed below, the "cavity value" determines the threshold or reference used to detect a sensed event or no sensed event condition.

If a sensed event was reported at block 122, the microprocessor proceeds from block 126 to block 128 as shown in FIG. 9D. At block 128, the microprocessor 40 sends out the programmed number of pulses to drive the transducer set for the active mode to generate the selected acoustic wave signal in the acoustic wave cavity for a scan, i.e. one sampling cycle. At block 128, prior to driving the transducer set for the active mode, the microprocessor controls the switches 51, 53 and 55 so that the correct transducer set is driven for the current active mode. Although as shown at block 120, the program number of pulses is typically between six to ten pulses. It should be apparent that more than ten pulses can be used to generate a resonant acoustic wave in the acoustic wave cavity during the first portion of the sampling cycle. After the microprocessor 40 controls the pulse generator 42 to output the programmed number of pulses via the switch 48 to the active transducer set for the first portion of a scan or sampling cycle, the microprocessor proceeds to block 130. At block 130, the microprocessor 40 loads, timer 1, which is an internal timer with the scan count time. The scan count time is the time during which the counter 46 is operable to count the output pulses from the comparator 44. Thereafter, at block 132, the microprocessor 40 clears the timer interrupt flag to allow a new interrupt to occur. The microprocessor 40 then proceeds from block 132 to block 134 to determine whether a hot level delay flag has been set. If so, the microprocessor at block 136 delays the start of the counter 46 by the programmed delay period so as to compensate for a highly sensitive acoustic wave cavity and to prevent an overflow of the counter 46. If the hot level delay flag has not been set as determined at block 134, the microprocessor 40 proceeds directly to block 138. The microprocessor 40 also proceeds from block 136 to block 138. At block 138, the microprocessor resets the counter 46, also designated timer 0. As soon as the counter 46 is reset to zero, the counter 46 starts counting the pulses output from the comparator 44. At block 140, the microprocessor 40 turns on the timer 1 for timing the scan count time. Thereafter, at block 142, the microprocessor returns from the current background process to continue the foreground process depicted in FIG. 8. This foreground process again will be interrupted when the timer 1 generates the timer 1 interrupt indicating that the scan count time for the current sampling cycle has been completed so that a new scan or sampling cycle can be started. As discussed above, the scan count time represents the second portion of the sampling cycle wherein the counter 46 is counting the pulses generated by the comparator 44.

Returning to FIG. 9B, if a no sensed event condition was reported at block 124 on the output Gp0, the microprocessor proceeds from block 126 to block 144 so as to update the "cavity value," i.e. the running average touch count value for a non-contacted acoustic wave cavity, so as to enable the touch threshold to be updated as well. The touch threshold is updated so as to compensate for drift due to changes in temperature, etc. At block 144, the microprocessor 40 determines whether the set level flag was previously set. The set flag is set to prevent a touch on the acoustic wave cavity during the initialization process from causing an error. If the flag was set, the microprocessor at block 146 sets the "cavity value" to the "touch count" measured for the current scan. Thereafter, at block 148, the microprocessor determines whether the hot level check flag was set and if so, at block 150 the microprocessor 40 calls the hot level check routine. The hot level check routine is implemented by the microprocessor at block 152 and if the timer 0 overflow flag has been set as a result of the hot level check routine or the touch count is greater than E0 Hex, then the microprocessor 40 sets the hot level delay flag at block 153. From either blocks 150 or 153, the microprocessor proceeds to block 154.

At block 154, the microprocessor 40 compares the "touch count" to the "cavity value." If the difference between the "touch count" and "cavity value" is greater than or equal to a predefined difference value, for example 5, then the microprocessor assumes that a change in the "cavity value" is needed at block 156. If a change is needed, the microprocessor at block 156 sets the "cavity value" to the current "touch count." Thereafter, at block 158, the microprocessor 40 compares the "touch count" to the "cavity value." If the two values are not equal, at block 160, the microprocessor determines the cavity direction. The cavity direction is up if the current "touch count" is greater than the "cavity value" and the direction is down if the "touch count" is less than the "cavity value." At block 162, the microprocessor 40 calculates the difference between the current "touch count" and the "cavity value." A "second difference count" is then incremented at block 164. The microprocessor at block 166, looks at the "second difference count" to determine which comparison value is to be used in the next step. If the "second difference count" is less than a "second difference compare" value which may be, for example, 48, the microprocessor proceeds from block 166 to block 168. However, if the "second difference count" is equal to the "second difference compare" value, i.e. 48, the microprocessor proceeds from block 166 to block 170. If the path from block 166 to block 168 is taken, the microprocessor at block 168 sets a difference compare to a primary level so that the microprocessor selects a "compare value" of for example 2 for a stainless steel acoustic wave cavity or 4 for an aluminum acoustic wave cavity, the compare value varying depending upon the material of the acoustic wave cavity 14. If the path from block 166 to block 170 is taken, at block 170, the microprocessor sets the difference compare to a secondary level. When set to the secondary level, the "compare value" is a calculated value and in particular is set equal to one-half of the "cavity value." From block 170, the microprocessor proceeds to block 172 to reset the "second difference count" to 0. The "second difference" correction allows slow adjustments to be made for larger than normal long term errors in the cavity value setting. From either blocks 172 or blocks 168, the microprocessor proceeds to block 174. At block 174, the microprocessor 40 compares the difference calculated at blocks 162 between the "touch count" and the "cavity value" to the "compare value" selected at either blocks 168 or block 170. If the difference calculated at block 162 is less than the selected compare value, the microprocessor proceeds from block 174 to block 176 to increment or decrement the cavity value depending on the cavity value direction set at block 160. In particular, if the cavity direction is up, the "cavity value" will be incremented at block 176. If the cavity direction set at block 160 is down, the "cavity value" will be decremented by one at block 176. This process at block 176 is a method of changing the "cavity value" so that it represents a running average of the touch count for a non-contacted acoustic wave cavity 14. It should be apparent that other methods of generating an average of the touch count can be used as well.

From block 176, the microprocessor proceeds to block 178 to update the threshold value representing the sensed event threshold or reference from a look up table that is associated with the material forming the acoustic wave cavity 14. It is noted that different look up tables can be used for the different modes of the sensor so that a different threshold or reference is selected to detect ice in the first mode than the threshold selected to detect water in the second mode. However, the same threshold can be used in both modes if desired. In a preferred embodiment, the look up table stores a number of threshold values corresponding to different "cavity values" or different cavity value ranges so that the threshold value will be selected based upon the "cavity value" determined at block 176. In this way, the touch threshold is updated so as to account for drift caused by temperature changes, etc. It is noted that instead of using a look up table, the threshold can be a value that is calculated as a function of the "cavity value." From block 178, the microprocessor 40 proceeds to block 180 so as to clear the "touch count," resetting the "touch count" value to zero in order for a new touch condition or no touch condition to be reported Gp0. If the microprocessor determines at block 174 that the difference calculated at block 162 is greater than the "compare value" determined at blocks 168 or 170, the "cavity value" and the threshold value are not updated. Instead, the microprocessor 40 proceeds directly to block 180 from block 174. From block 180, the microprocessor 40 proceeds to block 128 to trigger a new sampling cycle, i.e. a new scan as discussed above.

If the microprocessor 40 is in the diagnostic mode as determined at block 120, the diagnostic data reported at block 124, on an output pin of the controller 30 includes the following: the current sensed event or no sensed event condition of the acoustic wave cavity 12; the current value of the "touch count"; the current "cavity value"; the current value of the threshold; the low side cavity count determined at block 68; the high side cavity count as determined at block 76; and the "threshold adjustment" determined at block 78. The diagnostic data may be processed by another processor to which the controller 30 is coupled or the data may be transmitted to a remote computer for processing. Further, the microprocessor 40 may do various diagnostics on the data as well. In particular, a processor may compare the current touch count to a malfunction reference value to determine whether the switch has malfunctioned. For example, if the touch count is too high or too low signifying a malfunction, the processor performing the diagnostics generates a signal representing the malfunction of a particular switch. In response to the malfunction signal, a visual indication is provided by a display or the lighting of an LED or the like associated with the switch to indicate that the switch has malfunctioned. Alternatively, or in addition thereto, the processor performing the diagnostics may compare the "cavity value" representing an average of the "touch count" values to a reference to determine whether the switch has malfunctioned. In a further diagnostic test, the processor may determine a trend in the "touch count" values measured over a period of time or a trend in the "cavity values" measured over a period of time to determine a trend that may be indicative of a switch malfunction or of an impending switch malfunction. As a result of each of the diagnostics, the processor provides a signal indicative of the switch malfunction, the signal being used to control a display or light, an LED or the like to provide an indication that a switch has malfunctioned. It is noted, that the signal indicating switch malfunction may also be used to disable the malfunctioning sensor and enable another sensor.

The circuit of FIG. 7 may be used to drive and respond to a number of acoustic wave sensors that are located in an area of a structure where it is desired to detect the presence of ice and/or water. For example, 16 acoustic wave generators each associated with a different acoustic wave cavity and including the transducers for generating the different acoustic waves in the first and second modes, can be coupled to one controller 30. For applications having more than 16 acoustic wave sensors, one master processor may be coupled to and control a number of controllers 30, each of which is in turned coupled to a number of acoustic wave generators. Depending on the configuration of the controller used, a multiplexor may or may not be needed to handle multiple acoustic wave generators. If a multiplexor is used, the multiplexor is preferably disposed between the capacitor 32 and the transducers.

Many modifications and variations of the present invention are possible in light of the above teachings. For example, the acoustic wave sensor can be used to distinguish the presence of substances other than ice and water. Further, although the transducers in the first and second sets differ by at least one transducer to generate different acoustic waves, as used herein a transducer is different if its polarity is changed. For example, an electromagnetic transducer having a single coil with current flowing through the coil in one direction is considered different from the transducer using that same coil but where the current flow through the coil is in the opposite direction. Thus, it is to be understood that, within the scope of the appended claims, the invention may be practiced otherwise than as described hereinabove.

What is claimed is:

1. An ice detector comprising:
   an acoustic wave cavity formed in a substrate and defined by an area of increased mass;
   at least one transducer positioned adjacent to the acoustic wave cavity, the transducer when driven generating an acoustic wave trapped in the acoustic wave cavity, the acoustic wave being sensitive to the presence of ice on the acoustic wave cavity and insensitive to water on the acoustic wave cavity, and the transducer providing a signal representing the acoustic wave in the acoustic wave cavity; and
   a circuit responsive to the transducer signal to detect the presence of ice.

2. An ice detector as recited in claim 1 wherein the acoustic wave generated and trapped in the acoustic wave cavity is a torsional wave.

3. An ice detector as recited in claim 2 wherein the acoustic wave cavity has a planar surface and the transducer lies in a plane that is parallel to the planar surface.

4. An ice detector as recited in claim 1 wherein the transducer is a piezoelectric transducer mounted on a surface of the acoustic wave cavity off center with respect to the center of the cavity.

5. An ice detector as recited in claim 4 wherein the acoustic wave cavity is defined by an area of increased mass having a generally circular periphery and the transducer is positioned at a right angle to a radius of the cavity.

6. An ice detector as recited in claim 1 including at least two transducers positioned on opposite sides of a centerline of the cavity for generating the acoustic wave.

7. An ice detector as recited in claim 6 wherein the transducers are electro-magnetic transducers.

8. An ice detector as recited in claim 1 wherein the transducer is an electro-magnetic transducer positioned off center with respect to a centerline of the acoustic wave cavity.

9. An ice detector as recited in claim 1 wherein the circuit includes a comparator for comparing a value representing the acoustic wave signal to a reference to detect the presence of ice.

10. An ice detector as recited in claim 9 wherein the value represents a period of time the acoustic wave decays to a predetermined level.

11. A method of detecting ice comprising:
    forming an acoustic wave cavity in a substrate;
    generating an acoustic wave substantially trapped in said acoustic wave cavity wherein
    the acoustic wave in the cavity is sensitive to ice and insensitive to water;
    providing a signal representative of the acoustic wave in the acoustic wave cavity; and detecting the presence of ice on the acoustic wave cavity from the signal.

12. A method of detecting ice comprising:
generating a torsional acoustic wave substantially trapped in an acoustic wave cavity formed in a noncylindrical substrate, the presence of ice on a surface of the acoustic wave cavity producing a detectable change in the torsional acoustic wave; and
detecting the change in the torsional acoustic wave indicative of the presence of ice on a surface of the acoustic wave cavity.

13. A method of detecting ice comprising:
forming an acoustic wave cavity in a substrate defined by an area of increased mass;
generating a torsional acoustic wave substantially trapped in said acoustic wave cavity, the presence of ice on a surface of the acoustic wave cavity producing a detectable change in the torsional acoustic wave; and
detecting the change in the torsional acoustic wave indicative of the presence of ice on a surface of the acoustic wave cavity.

14. A method of detecting water and ice comprising:
generating an acoustic wave substantially trapped in an acoustic wave cavity wherein the acoustic wave in the cavity is insensitive to water and sensitive to ice;
providing a signal representative of the water insensitive acoustic wave in the acoustic wave cavity;
comparing the signal representing the water insensitive acoustic wave to a reference to detect the presence of ice on the acoustic wave cavity;
generating another acoustic wave substantially trapped in said acoustic wave cavity wherein the other acoustic wave is sensitive to water;
providing a signal representative of the water sensitive acoustic wave in the acoustic wave cavity; and
comparing the signal representing the water sensitive acoustic wave to a reference to detect the presence of water on the acoustic wave cavity.

15. A method of detecting water and ice comprising:
generating, in a first mode of operation, an acoustic wave substantially trapped in an acoustic wave cavity wherein the acoustic wave in the cavity is insensitive to water and sensitive to ice;
providing a signal representative of the water insensitive acoustic wave in the acoustic wave cavity;
generating, in a second mode of operation, another acoustic wave substantially tapped in an acoustic wave cavity wherein the other acoustic wave is sensitive to water;
providing a signal representative of the water sensitive acoustic wave in the acoustic wave cavity;
comparing the signal representing the water insensitive acoustic wave to a reference to detect the presence of ice on the acoustic wave cavity; and
comparing the signal representing the water sensitive acoustic wave to a reference to detect the presence of water on the acoustic wave cavity.

16. A method of detecting water and ice comprising:
positioning a plurality of transducers with respect to an acoustic wave cavity;
driving a first set of the transducers to generate an acoustic wave in the acoustic wave cavity wherein the acoustic wave in the cavity is sensitive to ice and insensitive to water;
providing a signal representing the acoustic wave generated by the first set of transducers;
driving a second set of the transducers to generate an acoustic wave in the acoustic wave cavity wherein the acoustic wave in the cavity is sensitive to water;
providing a signal representing the acoustic wave generated by the second set of transducers; and
analyzing the signals representing acoustic waves generated by the first and second sets of transducers to detect the presence of ice and/or water.

17. A method of distinguishing the presence of different substances on an acoustic wave sensor comprising:
generating, in a first mode of operation, a first acoustic wave substantially trapped in an acoustic wave cavity formed in the sensor, the first acoustic wave being sensitive to a first substance on the acoustic wave cavity;
generating, in a second mode of operation, a second acoustic wave, different from the first acoustic wave, substantially trapped in the acoustic wave cavity formed in the sensor, the second acoustic wave being sensitive to a second substance on the acoustic wave cavity; and
analyzing the response of the first and second acoustic waves to determine the presence of the first and/or second substances on the acoustic wave cavity.

18. A method as recited in claim 17 wherein the steps of generating the first and second acoustic waves in the acoustic wave cavity includes driving a first set of transducers positioned with respect to the acoustic wave cavity to generate the first acoustic wave and driving a second set of transducers positioned with respect to the acoustic wave cavity to generate the second acoustic wave.

19. A method as recited in claim 18 wherein the transducers in the first and second sets are different.

20. A method as recited in claim 18 wherein at least one of the transducers in the first set is not in the second set.

21. A method as recited in claim 18 wherein at least one of the transducers in the second set is not in the first set.

22. A method of distinguishing the presence of different substances on an acoustic wave sensor comprising:
positioning a plurality of transducers with respect to an acoustic wave cavity;
driving a first set of the transducers to generate in the acoustic wave cavity a first acoustic wave that is responsive to the presence of a first substance on the acoustic wave cavity;
providing a signal representing the first acoustic wave in the acoustic wave cavity;
driving a second set of the transducer to generate in the acoustic wave cavity a second acoustic wave that is responsive to the presence of a second substance on the acoustic wave cavity;
providing a signal representing the second acoustic wave in the acoustic wave cavity; and
analyzing the signals representing the first and second acoustic waves to detect the presence or absence of the first or second substances.

23. A method of detecting ice and water on a substrate comprising:
generating a torsional acoustic wave substantially trapped in an acoustic wave cavity formed in the substrate;
generating an acoustic wave other than a torsional acoustic wave in the acoustic wave cavity, the other acoustic wave being sensitive to water;
analyzing the response of the torsional acoustic wave and the other acoustic wave to determine the presence of ice and/or water.

24. A method as recited in claim 23 wherein the other acoustic wave generated includes shear wave components.

25. A method as recited in claim 23 wherein the other acoustic wave generated includes a flexural mode.

26. A method of detecting ice and water comprising:
positioning a first acoustic wave transducer centered on an acoustic wave cavity;
positioning a second acoustic wave transducer adjacent the acoustic wave cavity but off center with respect thereto;
driving the first acoustic wave transducer to generate in the acoustic wave cavity a first acoustic wave that is responsive to water;
driving the second acoustic wave transducer to generate in the acoustic wave cavity a second acoustic wave that is responsive to ice; and
analyzing the first and second acoustic waves to determine the presence of water and/or ice.

27. A method as recited in claim 26 including positioning a third acoustic wave transducer adjacent the acoustic wave cavity but off center with respect thereto wherein the third acoustic wave transducer is driven with the second acoustic wave transducer to generate in the acoustic wave cavity an acoustic wave that is responsive to ice.

28. A method of detecting the presence of different substances on an acoustic wave cavity formed in a substrate comprising:
positioning a first acoustic wave transducer adjacent the acoustic wave cavity but off center with respect thereto;
positioning a second acoustic wave transducer adjacent the acoustic wave cavity but off center with respect thereto;
driving the first acoustic wave transducer to generate a first acoustic wave responsive to a first substance on the acoustic wave cavity;
driving the first and second acoustic wave transducers to generate a second, different acoustic wave responsive to a second substance on the acoustic wave cavity; and
analyzing the first and second acoustic waves to determine the presence of the first and!or second substance.

29. A method of distinguishing the presence of different substances on an acoustic wave sensor comprising:
generating a first acoustic wave substantially trapped in an acoustic wave cavity formed in the sensor, the first acoustic wave having circular nodal lines and being sensitive to a first substance on the acoustic wave cavity;
generating a second acoustic wave substantially trapped in the acoustic wave cavity, the second acoustic wave having linear, parallel nodal lines and being sensitive to a second substance on the acoustic wave cavity; and
analyzing the response of the first and second acoustic waves to determine the presence of the first and/or second substances on the acoustic wave cavity.

30. A method as recited in claim 29 wherein the steps of generating the first and second acoustic waves in the acoustic wave cavity includes driving a first set of transducers positioned with respect to the acoustic wave cavity to generate the first acoustic wave and driving a second set of transducers positioned with respect to the acoustic wave cavity to generate the second acoustic wave.

31. A method as recited in claim 30 wherein the transducers in the first and second sets are different.

32. A method as recited in claim 30 wherein at least one of the transducers in the first set is not in the second set.

33. A method as recited in claim 30 wherein at least one of the transducers in the second set is not in the first set.

34. An ice detector comprising:
an acoustic wave cavity formed in a substrate and defined by an area of increased mass;
at least one transducer positioned adjacent the acoustic wave cavity, the transducer when driven generating in the acoustic wave cavity a torsional acoustic wave that is sensitive to ice, the transducer providing a signal representing the torsional acoustic wave in the acoustic wave cavity; and
a circuit responsive to the transducer signal to detect the presence of ice.

35. An ice detector as recited in claim 34 wherein the acoustic wave cavity has a planar surface and the transducer lies in a plane that is parallel to the planar surface.

36. An ice detector as recited in claim 35 wherein the transducer is a piezoelectric transducer mounted on a surface of the acoustic wave cavity off center with respect to the center of the cavity.

37. An ice detector as recited in claim 36 wherein the acoustic wave cavity is defined by an area of increased mass having a generally circular periphery and the transducer is position at a right angle to a radius of the cavity.

38. An ice detector as recited in claim 35 including at least two transducers positioned on opposite sides of a centerline of the cavity for generating the acoustic wave.

39. An ice detector as recited in claim 38 wherein the transducers are electro-magnetic transducers.

40. An ice detector as recited in claim 35 wherein the transducer is an electro-magnetic transducer positioned off center with respect to a centerline of the acoustic wave cavity.

41. An ice detector as recited in claim 35 wherein the circuit includes a comparator for comparing a value representing the acoustic wave signal to a reference to detect the presence of ice.

42. An ice detector as recited in claim 41 wherein the value represents a period of time the acoustic wave decays to a predetermined level.

43. An acoustic wave resonator comprising:
an acoustic wave cavity formed in a substrate and defined by an area of increased mass;
a plurality of transducers positioned adjacent said acoustic wave cavity;
a controller coupled to the transducers, the controller driving at least one transducer to generate a first acoustic wave in the acoustic wave cavity, the first acoustic wave being sensitive to ice and being insensitive to water and the controller driving at least one other transducer to generate a second acoustic wave in the acoustic wave cavity, the second acoustic wave being sensitive to water.

44. An acoustic wave resonator as recited in claim 43 wherein at least one of the transducers is centered on a centerline of the acoustic wave cavity.

45. An acoustic wave resonator as recited in claim 43 wherein at least one of the transducers is positioned off center with respect to a centerline of the cavity.

46. An acoustic wave resonator as recited in claim 43 wherein the plurality of the transducers includes at least two transducers positioned off center with respect to a centerline of the cavity and wherein the first set of transducers includes one of the off center transducers and the second set of transducers includes the two off center transducers.

47. An acoustic wave resonator as recited in claim 43 wherein the transducers in the first and second sets are different.

48. An acoustic wave resonator as recited in claim 43 wherein at least one of the transducers in the first set is not in the second set.

49. An acoustic wave resonator as recited in claim 43 wherein the polarity of at least one of the transducers in the first set is different from the polarity of the transducers in the second set.

50. An acoustic wave resonator as recited in claim 43 wherein at least one of the transducers in the second set is not in the first set.

51. An acoustic wave sensor comprising:
an acoustic wave cavity formed in a substrate and defined by an area of increased mass;
a plurality of transducers positioned adjacent the acoustic wave cavity;
a controller coupled to the transducers, the controller driving a first set of the transducers to generate a first acoustic wave in the acoustic wave cavity, the first acoustic wave being sensitive to ice and insensitive to water and the controller driving a second set of transducers to generate a second acoustic wave in the cavity, the second acoustic wave being sensitive to water and ice.

52. An acoustic wave sensor as recited in claim 51 wherein at least one of the transducers is centered on a centerline of the acoustic wave cavity.

53. An acoustic wave sensor as recited in claim 51 wherein at least one of the transducers is positioned off center with respect to a centerline of the cavity.

54. An acoustic wave sensor as recited in claim 51 wherein the plurality of the transducers includes at least two transducers positioned off center with respect to a centerline of the cavity and wherein the first set of transducers includes one of the off center transducers and the second set of transducers includes the two off center transducers.

55. An acoustic wave sensor as recited in claim 51 wherein the transducers in the first and second sets are different.

56. An acoustic wave sensor as recited in claim 51 wherein at least one of the transducers in the first set is not in the second set.

57. An acoustic wave sensor as recited in claim 51 wherein the polarity of at least one of the transducers in the first set is different from the polarity of the transducer in the second set.

58. An acoustic wave sensor as recited in claim 51 wherein at least one of the transducers in the second set is not in the first set.

59. An acoustic wave ice and water sensor comprising:
an acoustic wave cavity formed in a substrate and defined by an area of increased mass;
a plurality of transducers positioned adjacent the acoustic wave cavity including at least one transducer positioned off center with respect to a centerline of the cavity;
a controller coupled to the transducers, the controller driving a first set of the transducers including one off center transducer to generate a first acoustic wave in the acoustic wave cavity, the first acoustic wave being sensitive to ice and the controller driving a second set of transducers to generate a second acoustic wave in the acoustic wave cavity, the second acoustic wave being sensitive to water.

60. An acoustic wave ice and water sensor as recited in claim 59 wherein the first acoustic wave is a torsional acoustic wave.

61. An acoustic wave ice and water sensor as recited in claim 59 wherein the second acoustic wave is a shear wave.

62. An acoustic wave ice and water sensor as recited in claim 59 wherein the second set of transducers includes a transducer centered on the center of the acoustic wave cavity.

63. An acoustic wave ice and water sensor as recited in claim 59 wherein the second set of transducers includes the one off center transducer and a second off center transducer.

64. An acoustic wave ice and water sensor as recited in claim 63 wherein the polarity of the one off center transducer is in the same direction as the polarity of the second off center transducer, the one and second off centered transducers being positioned on opposite sides of a centerline of the acoustic wave cavity.

65. An acoustic wave ice and water sensor as recited in claim 59 wherein the first set of transducers includes at least one other off center transducer.

66. An acoustic wave ice and water sensor as recited in claim 59 wherein the controller is responsive to the receipt of a signal from at least one transducer in the first set for detecting the presence of ice and the controller is responsive to the receipt of a signal from at least one transducer in the second set for detecting the presence of water.

67. An acoustic wave ice and water sensor as recited in claim 66 wherein the controller switches from driving the first set of transducers to driving the second set of transducers after detecting the presence or absence of ice on the acoustic wave cavity.

68. An acoustic wave ice and water sensor as recited in claim 66 wherein the controller switches from driving the second set of transducers to driving the first set of transducers after detecting the presence or absence of water on the acoustic wave cavity.

69. An acoustic wave ice and water sensor as recited in claim 59 wherein the acoustic wave cavity is formed in a substrate that is an insert for mounting in an aperture of a structure.

70. An acoustic wave ice and water sensor as recited in claim 59 wherein the structure is an insert support having threads on a portion of an outer surface thereof.

71. An acoustic wave ice and water sensor as recited in claim 59 wherein the structure is a member of a device for which ice detection is desired.

72. An ice detector for a structure comprising:
an acoustic wave cavity formed in a substrate, the substrate being an insert for mounting in an aperture of the structure;
at least one transducer mounted adjacent the acoustic wave cavity, the transducer when driven generating an acoustic wave trapped in the acoustic wave cavity, the acoustic wave being sensitive to the presence of ice on a surface of the acoustic wave cavity and the transducer providing a signal representing the acoustic wave in the acoustic wave cavity; and
a circuit responsive to the transducer signal to detect the presence of ice on a surface of the acoustic wave cavity.

73. An ice detector as recited in claim 72 wherein the substrate is a first insert mounted in a support, the support forming a second insert for mounting in the aperture of the structure.

74. An ice detector as recited in claim 73 wherein the support includes a head portion with an aperture therein for receiving the substrate with the acoustic wave cavity and the support having a body extending from the head portion, the body extending through the aperture of the structure when mounted therein.

75. An ice detector as recited in claim 74 wherein the body includes threads on at least an outer portion thereof.

76. An ice detector as recited in claim 74 wherein the body is hollow and the transducers are mounted in the hollow portion of the body.

77. An ice detector as recited in claim 76 wherein at least a portion of the circuit is mounted in the hollow portion of the body.

78. An ice detector as recited in claim 72 wherein the insert includes a head portion in which the acoustic wave cavity is formed and the insert has a body extending from the head portion, the body extending through the aperture of the structure when mounted therein.

79. An ice detector as recited in claim 78 wherein the body includes threads on at least an outer portion thereof.

80. An ice detector as recited in claim 78 wherein the body is hollow and the transducers are mounted in the hollow portion of the body.

81. An ice detector as recited in claim 78 wherein at least a portion of the circuit is mounted in the hollow portion of the body.

82. An ice and water detector comprising:
    an acoustic wave cavity formed in a substrate and defined by an area of increased mass;
    a plurality of transducers positioned adjacent the acoustic wave cavity, a first set of the transducers when driven generating in the acoustic wave cavity, a first acoustic wave that is sensitive to ice on a surface of the acoustic wave cavity and insensitive to water on a surface of the acoustic wave cavity and a second set of the transducers when driven generating in the acoustic wave cavity, a second acoustic wave that is sensitive to water;
    a controller responsive to signals respectively representing the first and second acoustic waves in the acoustic wave cavity to determine the presence of ice and!or water on a surface of the acoustic wave cavity.

* * * * *